US006448058B1

(12) United States Patent
Patel et al.

(10) Patent No.: US 6,448,058 B1
(45) Date of Patent: Sep. 10, 2002

(54) METHODS FOR SOLID PHASE SYNTHESIS OF MERCAPTO COMPOUNDS AND DERIVATIVES, COMBINATORIAL LIBRARIES THEREOF AND COMPOSITIONS OBTAINED THEREBY

(75) Inventors: Dinesh V. Patel, Fremont, CA (US); Khehyong Ngu, Lawrenceville, NJ (US); Jianping Zhou, Mountain View, CA (US)

(73) Assignee: Versicor, Inc., Fremont, CA (US)

( * ) Notice: Subject to any disclaimer, the term of this patent is extended or adjusted under 35 U.S.C. 154(b) by 0 days.

(21) Appl. No.: 09/151,608

(22) Filed: Sep. 11, 1998

Related U.S. Application Data

(60) Provisional application No. 60/058,744, filed on Sep. 12, 1997.

(51) Int. Cl.$^7$ .................................. C12N 9/18
(52) U.S. Cl. ........................................ 435/197
(58) Field of Search .......................... 435/197

(56) References Cited

U.S. PATENT DOCUMENTS

| | | | |
|---|---|---|---|
| 5,525,734 A | 6/1996 | Gallop et al. |
| 5,525,735 A | 6/1996 | Gallop et al. |
| 5,549,974 A | 8/1996 | Holmes |
| 5,691,162 A | 11/1997 | Shuster et al. |

FOREIGN PATENT DOCUMENTS

| | | |
|---|---|---|
| EP | 0 322 184 | 6/1989 |
| WO | WO 95/35278 | 12/1995 |

OTHER PUBLICATIONS

Guo et al., "A Direct Spectrophotometric Assay for Peptide Deformylase", Anal. Biochem. (Sep. 1999), 273(2), 298–304.*
Huntington et al., "Synthesis and Antibacterial Activity of Peptide Deformylase Inhibitors", Biochemistry (Apr. 18, 2000), 39(15), 4543–4551.*
Adams, J.M., "On the Release of the Formyl Group from Nascent Protein" (1968) J. Mol. Biol., 33(3), 571–589.*
Becker et al. "Structure of Peptide Deformylase and Identification of the Substrate Binding Site" (May, 1998) J. Biol. Chem., 273(19), 11413–11416.*
Bartlett et al., "Phosonamidates as Transition–State Analogue Inhibitors of Thermolysin" (1983) Biochemistry, 22(20), 4618–4624.*
Apfel et al., "Hydroxamic Acid Derivatives as Potent Peptide Deformylase Inhibitors and Antibacterial Agents" (2000) J. Med. Chem., 43(12), 2324–2331.*
Becker et al., "Iron Center, Substrate Recognition and Mechanism of Peptide Deformylase" (Dec., 1998) Nature Struct. Biol., 5(12), 1053–1058.*

Wei et al., "Identification of a Potent Peptide Deformylase Inhibitor from a Rationally Designed Combinatorial Library" (2000) J. Comb. Chem., 2(6), 650–657.*
Albericio et al., "Preparation and application of the 5-(4-(9-fluorenylmethyloxycarbonyl)aminomethyl-3, 5-dimethoxyphenoxy)-valeric acid (PAL) handle for the solid–phase synthesis of C-terminal peptide amides under mild conditions" (1990) J. Org. Chem. 55:3730–3743.
Albericio et al., "Hypersensitive acid–labile (HAL) tris-(alkoxy)benzyl ester anchoring for solid–phase synthesis of protected peptide segments" (1991) Tet. Lett. 32:1015–1018.
Baici et al., "A handy assay for collagenase using reconstituted fluorescein–labeled collagen fibrils" (1980) Anal. Biochem. 108:230–232.
Balkenhohl et al., "Combinatorial synthesis of small organic molecules" (1996) Angew. Chem. Int. Ed. Engl. 35:2289–2337.
Birkedal–Hansen et al., "Matrix metalloproteinases: A review" (1993) Crit. Rev. Oral Biol. Med. 4:197–250.
Borden et al., "Transcriptional control of matrix metalloproteinases and the tissue inhibitors of matrix metalloproteinases" (1997) Critical Reviews in Eukaryotic Gene Expression 7:159–178.
Botti et al., "Cyclic peptides from linear unprotected peptide precursors throgh thiazolidine formation" (1996) J. Am. Chem. Soc. 118:10018–10024.
Brown, Peter D., "Matrix metalloproteinase inhibitors: A novel class of anticancer agents" (1995) Advan. Enzyme Regul. 35:293–301.
Brown et al., "Matrix metalloproteinase inhibition: A review of anti–tumor activity" (1995) Ann. Oncol. 6:967–974.
Bunin et al., "A general and expedient method for the solid–phase synthesis of 1,4–benzodiazepine derivatives" (1992) J. Am. Chem. Soc. 114:10997–10998.
Bush et al., "Kinetic interactions of tazobactam with β–lactamases from all major structural classes" (1993) Antimicrobial Agents and Chemotherapy 37:851–858.
Canne et al., "A general method for the synthesis of thioester resin linkers for use in the solid phase synthesis of peptide–α–thioacids" (1995) Tetrahedron Lett. 36:1217–1220.
Cawston et al., "A rapid and reproductive assay for collagenase using [1–$^{14}$C]acetylated collagen" (1979) Anal. Biochem. 99: 340–345.
Cawston et al., "Purification of rabbit bone inhibitor of collagenase" (1981) Biochem. J. 195:159–165.

(List continued on next page.)

Primary Examiner—Jon P. Weber
(74) Attorney, Agent, or Firm—Morrison & Foerster LLP

(57) ABSTRACT

Methods of preparing combinatorial libraries of mercapto (thiol) compounds them and compositions obtained therefrom are disclosed. The compounds are synthesized on a solid support. Following synthesis, the compounds are optionally cleaved from the support. One such method of synthesis involves attack of an S-protected nucleophile on a resin functionalized with a leaving group. The invention also provides for screening the mercapto compounds for bioactive compounds; in particular, for inhibitors of MMPs.

3 Claims, 1 Drawing Sheet

OTHER PUBLICATIONS

Cawston et al., "Mammalian collagenases" (1981) *Methods in Enzymology* vol. 80, Academic Press, New York. Chapter 52, pp. 711–722.

Chan et al., "Crystal structure of the *Escherichia coli* peptide deformylase" (1997) *Biochem.* 36:13904–13909.

Chang et al., "Methionine aminopeptidase gene of *Escherichia coli* is essential for cell growth" (1989) *J. Bacteriol.* 171:4071–4072.

Cho et al., "An unnatural biopolymer" (1993) *Science* 261:1303–1305.

Coussens et al., "Matrix metalloproteinases and the development of cancer" (1996) *Chemistry & Biology* 3:895–904.

Daub et al., Isolation, cloning, and sequencing of the *Salmonella typhimurium* ddlA gene with purification and characterization of its product, D–alamine:D–alanine ligase (ADP forming) (1988) *Biochemistry* 27:3701–3708.

DiPasquale et al., "Proteoglycan–and collagen–degrading enzymes from human interleukin 1–stimulated chondrocytes from several species: Proteoglycanase and collagenase inhibitors as potentially new disease–modifying antiarthritic agents (42416)" (1986) *Proc. Soc. Exp. Biol. Med.* 183:262–267.

Evans et al., "The assymmetric synthesis of α–amino acids. Electrophilic azidation of chiral imide enolates, a practical approach to the synthesis of (R) and (S)–α–azido carboxylic acids" (1990) *J. Amer. Chem. Soc.* 112:4011–4030.

Flösheimer et al., "Solid–phase synthesis of peptides with the highly acid–sensitive HMPB linker" Peptides 1990: Proceedings of the 21st European Peptide Symposium (Giralt and Andreu, eds.); Leiden: ESCOM Science Publishers B.V. (1991) pp 131–133.

Fodor et al., "Light–directed, spatially addressable parallel chemical synthesis" (1991) *Science* 251:767–773.

Furka et al., "General method for rapid synthesis of multi-component peptide mixtures" (1991) *Int. J. Peptide Protein Res.* 37:487–493.

Geysen et al., "Use of peptide synthesis to probe viral antigens for epitopes to a resolution of a single amino acid" (1984) *Proc. Natl. Acad. Sci. USA* 81: 3998–4002.

Goetzl et al., "Matrix metalloproteinases in immunity" (1996) *J. Immunol.* 156:1–4.

Gordon, Eric M., "Libraries of non–polymeric organic molecules" (1995) *Curr. Op. Biotechnol.* 6:624–631.

Gordon et al., "Reductive alkylation on a solid phase: Synthesis of a piperazinedione combinatorial library" (1995) *Bioorg. Medicinal Chem. Lett.* 5:47–50.

Gordon et al.,"Strategy and tactics in combinatorial organic synthesis: Applications to drug discovery" (1996) *Acc. Chem. Res.* 29:144–154.

Grant et al., "Collagenolytic protease from fiddler crab (*Uca pugilator*)" (1981) *Methods in Enzymology* vol. 80, Academic Press, New York. Chapter 53, pp. 722–734.

Harper et al., "Amino acids & peptides" (1977) *Review of Physiological Chemistry,* 16th Ed., Lange Medical Publications, pp. 21–24.

Häse et al.,"Bacterial extracellular zinc–containing metalloproteases" (1993) *Microbiol. Rev.* 57:823–837.

Heimer et al., "Small–ring heterocyclic compounds. IV. Attempted synthesis of 1,2,–thiazetidines and thiazetes," (1970) *Journal of Organic Chemistry* 35(5):1668–1670.

Hoeg–Jensen et al., "Amino monothio acids in solid–phase synthesis of peptide thioamides" (1996) *Int. J. Peptide Protein Res.* 47:190–200.

Holmes et al., "Strategies for combinatorial organic synthesis: Solution and polymer–supported synthesis of 4–thiazolidinones and 4–metathiazanones derived from amino acids" (1995) *J. Org. Chem.* 60:7328–7333.

Houghten et al., "General method for the rapid solid–phase synthesis of large numbers of peptides: Specificity and antigen–antibody interaction at the level of individual amino acids" (1985) *Proc. Natl. Acad. Sci. USA* 82:5131–5135.

Jia et al., "Snake venom metalloproteinases: Structure, function and relationship to the ADAMS family of proteins" (1996) *Toxicon* 34:1269–1276.

Kamiguti et al., "Insights into the mechanism of haemorrhage caused by snake venom metalloproteinases" (1996) *Toxicon* 34:627–642.

Keating et al., "Postcondensation modifications of Ugi four–component condensation products: 1–Isocyanocyclohexene as a convertible isocyanide. Mechanism of conversion, synthesis of diverse structures, and demonstration of resin capture" (1996) *J. Am. Chem. Soc.* 118:2574–2583.

Kemp et al., "Peptide synthesis by prior thiol capture. 1. A convenient synthesis of 4–hydroxy–6–mercaptodibenzofuran and novel solid–phase synthesis of peptide–derived 4-(acyloxy)–6–mercaptodibenzofurans" (1986) *J. Org. Chem.* 51:1821–1829.

Kooi et al., "Differentiation of thermolysins and serralysins by monoclonal antibodies" (1996) *J. Med. Microbiol.* 45:219–225.

Liotta et al., "Cancer metastasis and angiogenesis: An imbalance of positive and negative regulation" (1991) *Cell* 64:327–336.

Long et al., Regulation of extracellular alkaline protease activity by histidine in a collagenolytic *Vibrio alginolyticus* strain (1981) *J. Gen. Microbiol.* 127:193–199.

Matrisian, Lynn M., "Metalloproteinases and their inhibitors in matrix remodeling" (1990) *Trends in Genetics* 6:121–126.

McConn et al., "*Bacillus subtilis* neutral proteinase" (1964) *J. Biol. Chem.* 239:3706–3715.

McDermott et al., "Human brain peptidase activity with the specificity to generate the n–terminus of the Alzheimer β–amyloid protein from its precursor" (1992) *Biochem. Biophys. Res. Comm.* 185:746–753.

McDonnell et al., "Stromelysin in tumor progression and metastasis" (1990) *Cancer and Metastasis Review* 9:305–319.

Meinnel et al., "Characterization of the *Thermus thermophilus* locus encoding peptide deformylase and methionyl––tRNA$_{fMet}$ formyltransferase" (1994) *J. Bacteriol.* 176:7387–7390.

Meinnel et al., "A new subclass of the zinc metalloproteases superfamily revealed by the solution structure of peptide deformylase" (1996) *J. Mol. Biol.* 262:375–386.

Meinnel et al., "Structure–function relationships within the peptide deformylase family. Evidence for a conserved architecture of the active site involving three conserved motifs and a metal ion" (1997) *J. Mol. Biol.* 267:749–761.

Minami et al., "Lambda–toxin of *Clostridium perfringens* activates the precursor of epsilon–toxin by releasing its N–and C–terminus peptides" (1997) *Microbiol. Immunol.* 41:527–535.

Miyata et al., "Serratia protease. Part III. Characteristics of the enzyme as metalloenzyme" (1971) *Agr. Biol. Chem.* 35:460–467.

Moffat et al., "Further molecular characterization of the cloned *Legionella pneumophila* zinc metalloprotease" (1994) *Infection and Immunity* 62:751–753.

Murphy et al., "The detection and characterisation of collagenase inhibitors from rabbit tissues in culture" (1977) *Bioch. Biophys. Acta* 483:493–498.

Murphy et al., "Proteinases in rheumatoid arthritis" (1992) *J. Rheumatol.* (suppl. 32) 19:61–64.

Murphy et al., "Combinatorial organic synthesis of highly functionalized pyrrolidines: Identification of a potent angiotensin converting enzyme inhibitor from a mercaptoacyl proline library" (1995) *J. Am. Chem. Soc.* 117:7029–7030.

Ngu et al., "Preparation of acid–labile resins with halide linkers and their utility in solid phase organic synthesis" (1997) *Tet. Lett.* 38:973–976.

Okamoto et al., "Activation of human matrix metalloproteinases by various bacterial proteinases" (1997) *J. Biol. Chem.* 272:6059–6066.

Onishi et al., "Antibacterial agents that inhibit lipid A biosynthesis" (1996) *Science* 274:980–982.

Papastoitsis et al., "Identification of a metalloprotease from Alzheimer's disease brain able to degrade the β–amyloid precursor protein and generate amyloidogenic fragments" (1994) *Biochem.* 33:192–199.

Pu et al., "Synthesis and acylation of salts of L–threonine β–lactone: A route to β–lactone antibiotics" (1991) *J. Org. Chem..* 56:1280–1283.

Rajagopalan et al., "Peptide deformylase: A new type of mononuclear iron protein" (1997) *J. Am. Chem. Soc.* 119:12418–12419.

Rajagopalan et al., "Purification, characterization, and inhibition of peptide deformylase from *Escherichia coli*" *Biochemistry* (1997) 36:13910–13918.

Rosenberg et al., "Tumor necrosis factor–α–induced gelatinase B causes delayed opening of the blood–brain barrier: an expanded therapeutic window" (1995) *Brain Res.* 703:151–155.

Schwartz et al., "Synthetic inhibitors of bacterial and mammalian interstitial collagenases" (1992) *Progress in Medicinal Chemistry* 29 Elsevier, New York, Chapter 8 pp. 271–334.

Sekine, Hiroshi, "Neutral proteinases" (1973) *Agric. Biol. Chem.* 37:1945–1952.

Sellers et al., "Evidence that latent collagenases are enzyme–inhibitor complexes" (1977) *Biochem J.* 163:303–307.

Sellers et al., "Identification and partial characterization of an inhibitor of collagenase from rabbit bone" (1977) *Biochem. J.* 167:353–360.

Sellers et al., "Neutral metallo–proteinases of rabbit bone" (1978) *Biochem. J.* 171: 493–496.

Sharma et al., "Reductive amination with tritylamine as an ammonia equivalent: Efficient preparation of the 5–[[(9–fluorenylmethyloxycarbonyl)–amino]methyl]–3, 5–dimethoxyphenoxy]valeric acid (PAL) handle for peptide synthesis" (1993) *J. Org. Chem.* 58:4993–4996.

Simon et al., "Peptoids: A modular approach to drug discovery" (1992) *Proc. Natl. Acad. Sci. USA* 89:9367–9371.

Smith et al., "Solid and solution phase organic synthesis of oligomeric thioureas" (1996) *J. Org. Chem.* 61:8811–8818.

Stöcker et al., "The metzincins—topical and sequential relations between the astacins, adamalysins, serralysins, and matrixins (collagenases) define a superfamily of zinc–peptidases" (1995) *Protein Sci.* 4: 823–840.

Takahashi et al., "Substrate specificity of a novel alcohol resistant metalloproteinase, vimelysin, from Vibrio sp. T 1800" *Biosci. Biotech. Biochem.* 60:1651–1654.

Takino et al., "Identification of the second membrane–type matrix metalloproteinase (MT–MMP–2) gene from a human placenta cDNA library" (1995) *J. Biol. Chem.* 270:23013–23020.

Thompson, Robert W., "Basic science of abdominal aortic aneurysms: emerging therapeutic strategies for an unresolved clinical problem" (1996) *Curr. Opin. Cardiol.* 11:504–518.

Turner et al., "Mammalian membrane metallopeptidases: NEP, ECE, KELL, and PEX" (1997) FASEB J. 11:355–364.

Vallee et al., "Zinc coordination, function, and structure of zinc enzymes and other proteins" (1990) *Biochem.* 29:5647–5659.

Wang, Su–Sun, p–alkoxybenzyl alcohol resin and p–alkoxybenzyloxycarbonlhydrazide resin for solid phase synthesis of protected peptide from fragments (1973) *J. Am. Chem. Soc.* 95:1328–1333.

Wei et al., "Continuous spectrophotometric assay of peptide deformylase" (1997) *Anal. Biochem.* 250:29–34.

Will et al., "cDNA sequence and mRNA tissue distribution of a novel human matrix metalloproteinase with a potential transmembrane segment" (1995) *Eur. J. Biochem.* 231:602–608.

Williams et al., "Asymmetric synthesis of monosubstituted and αα–disubstituted α–amino acids via diastereoselective glycine enolate alkylations" *J. Amer. Chem. Soc.* 113:9276–9286.

Zaragoza, Florencio, "Solid phase synthesis of substituted 3–aminothiophenes and 2–methylene–2,3–dihydrothiazoles" (1997) *Tetrahedron Lett.* 37:6213–6216.

\* cited by examiner

METHODS FOR SOLID PHASE SYNTHESIS OF MERCAPTO COMPOUNDS AND DERIVATIVES, COMBINATORIAL LIBRARIES THEREOF AND COMPOSITIONS OBTAINED THEREBY

CROSS-REFERENCE TO RELATED APPLICATIONS

This application claims priority benefit of co-pending U.S. provisional patent application No. 60/058,744 filed Sep. 12, 1997. The content of that application is hereby incorporated by reference herein in its entirety.

STATEMENT OF RIGHTS TO INVENTIONS MADE UNDER FEDERALLY SPONSORED RESEARCH

Not applicable.

TECHNICAL FIELD

This invention is directed to methods for producing combinatorial chemistry libraries containing mercapto (thiol) compounds and derivatives. This invention is further directed to synthesis of combinatorial chemistry libraries of mercapto compounds and derivatives using solid-phase techniques. This invention is still further directed to the libraries of mercapto compounds and derivatives produced by the synthetic methods disclosed. This invention is still further directed to utilizing the libraries of mercapto compounds and derivatives thereof to identify and select compounds which bind to, inhibit, or otherwise affect enzymes, receptors, or other biological molecules implicated in disease processes (including disease-related metalloproteinases). The mercapto compounds and derivatives thus selected are suitable for use as therapeutics.

BACKGROUND ART

The techniques of combinatorial chemistry have been increasingly exploited in the process of drug discovery. Combinatorial chemistry allows for the synthesis of a wide range of compounds with varied molecular characteristics. Combinatorial synthetic techniques enable the synthesis of hundreds to millions of distinct chemical compounds in the same amount of time required to synthesize one or a few compounds by classical synthetic methods. Subjecting these compounds to high-throughput screening allows thousands of compounds to be rapidly tested for desired activity, again saving time, expense and effort in the laboratory.

Chemical combinatorial libraries are diverse collections of molecular compounds. Gordon et al. (1995) *Acc. Chem. Res.* 29:144–154. These compounds are formed using a multistep synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

For several reasons, the initial work in combinatorial library construction focused on peptide synthesis. Furka et al. (1991) *Int. J. Peptide Protein Res.* 37:487–493; Houghten et al. (1985) *Proc. Natl. Acad. Sci. USA* 82:5131–5135; Geysen et al. (1984) *Proc. Natl. Acad. Sci. USA* 81: 3998–4002; and Fodor et al. (1991) *Science* 251:767. The rapid synthesis of discrete chemical entities is enhanced where the need to purify synthetic intermediates is minimized or eliminated; synthesis on a solid support serves this function. Construction of peptides on a solid support is well-known and well-documented. Obtaining a large number of structurally diverse molecules through combinatorial synthesis is furthered where many different chemical modules are readily available; hundreds of natural and non-natural amino acid modules are commercially available. Finally, many peptides are biologically active, making them suitable for use as a class to the pharmaceutical industry.

The scope of combinatorial chemistry libraries has recently been expanded beyond peptide synthesis. Polycarbamate and N-substituted glycine libraries have been synthesized in an attempt to produce libraries containing chemical entities that are similar to peptides in structure, but possess enhanced proteolytic stability, absorption and pharmacokinetic properties. Cho et al. (1993) *Science* 261:1303–1305; and Simon et al. (1992) *Proc. Natl. Acad. Sci. USA* 89:9367–9371. Furthermore, benzodiazepine, pyrrolidine, and diketopiperazine libraries have been synthesized, expanding combinatorial chemistry to include heterocyclic entities. Bunin et al. (1992) *J. Am. Chem. Soc.* 114:10997–10998; Murphy et al. (1995) *J. Am. Chem. Soc.* 117:7029–7030; and Gordon et al. (1995) *Bioorg. Medicinal Chem. Lett.* 5:47–50.

Mercapto compounds have received a great deal of attention as inhibitors of matrix metalloproteinases (MMPs), a class of enzymes that acts on components of the extracellular matrix and basement membranes, such as collagen, fibronectin, and laminin. Borden et al. (1997) *Critical Reviews in Eukaryotic Gene Expression* 7:159. The extracellular matrix plays a role in a wide variety of biological processes, such as cell proliferation, cell differentiation, cell adhesion, cell migration, and tissue morphogenesis. Matrisian (1990) *Trends in Genetics* 6:121. Metalloproteinases are members of a superfamily of enzymes which share a number of features. Their activity depends on the peptide nature of their substrates; full enzymatic activity requires a metal ion (generally zinc, cobalt, or iron) bound by the side chains of conserved amino acids at or near the active site; among the conserved metal-binding residues are histidines belonging to a motif, HEXXH (SEQ ID NO:1). The enzymes are sensitive to metal-chelating reagents. Vallee and Auld (1990) *Biochem.* 29:5647–5659; and Stöcker et al. (1995) *Protein Sci.* 4: 823–840. Currently, the family comprises two subclasses, exemplified by thermolysin and metzincins.

The metalloproteinase superfamily encompasses metalloproteinases from a wide variety of organisms. For example, matrix metalloproteinases in mammals act to modify or degrade extracellular matrix components such as collagens, fibronectin, and laminin. Birkedal-Hansen et al. (1993) *Crit. Rev. Oral Biol. Med.* 4:197–250. MMP's are believed to be involved in the development of arthritis, tumor angiogenesis, retinopathy, and many other disease processes. While many MMP's are secreted from the cell, others remain membrane bound. Takino et al. (1995) *J. Biol. Chem.* 270:23013–23020; Will and Hinzmann (1995) *Eur. J. Biochem.* 231:602–608; and Turner and Tanzawa (1997) *FASEB J.* 11:355–364. Other metalloproteinases isolated from mammals include endopeptidase EC 3.4.24.15, which is believed to be involved in the regulated metabolism of a number of neuropeptides (Papastoitsis et al. (1994) *Biochem.* 33:192–199; and McDermott et al. (1992) *Biochem. Biophys. Res. Comm.* 185:746–753); angiotensin-converting enzyme; endothelin-converting enzyme; and neutral endopeptidase. Homologues of these various human metalloproteinases have been reported in a variety of animal species. Snake venom metalloproteinases also degrade major proteins of the extracellular matrix, and further have been reported to degrade platelet integrin VLA-2 and von Willebrand factor. Jia et al. (1996) *Toxicon* 34:1269–1276; and Kamiguti et al. (1996) *Toxicon* 34:627–642. Fungi such as Aspergillus and Fusarium have been reported to synthesize metalloproteinases. Sekine (1973) *Agric. Biol. Chem.* 37:1945–1952; and U.S. Pat. No. 5,691,162. Metalloproteinases have also been isolated from parasitic organisms which can be pathogenic toward mammals, including protozoan parasites such as helminths (U.S. Pat. No. 5,691,186). Bacteria also synthesize metalloproteinases. Hase et al. (1993) *Microbiol. Rev.* 57:823–837. Metalloproteinases have been isolated from various bacteria including Bacillus species such as *Bacillus subtilis* (McConn et al. (1964) *J. Biol. Chem.* 239:3706); Serratia (Miyata et al. (1971) *Agr. Biol. Chem.* 35:460); *Legionella pneumophila* (Moffat et al. (1994) *Infection and Immunity* 62:751–753); Vibrio species (Takahashi et al. (1996) *Biosci. Biotech. Biochem.* 60:1651–1654; and Clostridium species such as *Clostridium perfringens* (Minami et al. (1997) *Microbiol. Immunol.* 41:527–535. Activities of some of these enzymes can produce deleterious effects in mammals. For example, the λ-toxin of *C. perfringens* acts to cleave and activate another toxin produced by this bacterium. Minami et al. (1997). Other bacterial metalloproteinases can act to activate zymogen forms of human MMP's. Okamoto et al. (1997) *J. Biol. Chem.* 272:6059–6066.

A relatively new member of the metalloproteinase superfamily is the bacterial enzyme peptide deformylase (PDF). In bacteria, nascent proteins typically contain an N-formyl group on the N-terminal methionine. This enzyme catalyzes removal of the formyl moiety from nascent proteins, and this activity is essential for maturation of nascent proteins. Deformylase activity is critical to the growth of *Escherichia coli*. Chang et al. (1989) *J. Bacteriol.* 171:4071–4072; and Meinnel and Blanquet (1994) *J. Bacteriol.* 176:7387–7390. While this enzyme clearly shares many of the features which characterize metalloproteinases, it differs from other members of the superfamily in several important respects. Firstly, the metal ion in the active enzyme appears to be Fe(II), or possibly another divalent cationic metal, instead of the zinc ion more commonly encountered. Rajagopalan et al., (1997) *J. Am. Chem. Soc.*, 119:12418–19. Secondly, the divalent ion appears to play an important role, not only in catalysis, but also in the structural integrity of the protein; thirdly, the third ligand of the divalent ion is a cysteine, rather than a histidine or a glutamate, as in other metalloproteinases; fourthly, this third ligand is not located at the C-terminal side of the HEXXH (SEQ ID NO:1) motif but far away along the amino acid sequence, and N-terminal to the motif; finally, the solution structure shows significant differences in the secondary and tertiary structure of PDF, compared with other prototypical metalloproteinases. Meinnel et al. (1996) *J. Mol. Biol.* 262:375–386. PDF from *E. coli, Bacillus stearothermophilus*, and *Thermus thermophilus* have been characterized. Meinnel et al. (1997) *J. Mol. Biol.* 267:749–761. The enzyme studied by Meinnel et al. contained a zinc ion as the divalent ion, and the structural features summarized above were obtained from zinc-containing proteins.

MMPs present an attractive target for therapy in a wide variety of disorders due to the role they play in both normal and pathological physiological processes. These pathologies include tumor growth, invasion and metastasis (Coussens et al. (1996) *Chemistry & Biology* 3:895; Brown et al. (1995) *Ann. Oncol.* 6:967; and McDonnell et al. (1990) *Cancer and Metastasis Review* 9:305); angiogenesis during cancer development (Liotta et al. (1991) *Cell* 64:327); abdominal aortic aneurysms (Thompson, (1996) *Curr. Opin. Cardiol.* 11:504); inflammation (Goetzl et al. (1996) *J. Immunol.* 156:1); and arthritis (Murphy et al. (1992) *J. Rheumatol. (suppl.* 32) 19:61). Gelatinase A (Type IV collagenase) has been implicated in breaching the blood-brain barrier during hemorrhagic brain injury (Rosenberg et al. (1995) *Brain Res.* 703:151). Other potential enzyme targets of clinical interest include microbial enzymes (Onishi et al.(1996) *Science* 274:980).

Because of the wide variety of potential clinical applications for MMP inhibitors, much attention has been focused on developing such inhibitors. Brown (1995) *Advan. Enzyme Regul.* 35:293. Thiol-based collagenase inhibitors are reported in Johnson et al. (1987) *J. Enzyme Inhibition* 2:1. Mercapto inhibitors of collagenase and stromelysin inhibitors are described in Wahl et al. Chapter 19 of *Annual Reports in Medicinal Chemistry*, Vol. 25, Academic Press, San Diego, 1989. Thiol inhibitors of proteoglycanases and collagenases are disclosed in DiPasquale et al. (1986) *Proc. Soc. Exp. Biol. Med.* 183:262. Thiol and other inhibitors of collagenases are described in Schwartz et al. Chapter 8 in *Progress in Medicinal Chemistry*, vol. 29, Elsevier, N.Y., 1992.

With one important exception, efforts in the field of combinatorial chemistry have not focused on mercapto compounds (thiol-containing compounds). This exception is, of course, peptides containing cysteine residues and analogs such as homocysteine. The free side chain of cysteine contains a mercapto (thiol) group, and hence a cysteine-containing peptide can be considered a mercapto compound. If compounds which have thiol groups provided solely by one or more cysteine, homocysteine, or other cysteine analogs are excluded from the purview of mercapto libraries, however, the field is substantially narrowed.

One previous effort in generating combinatorial libraries of mercapto compounds on a solid support is presented in Murphy et al. (1995) *J. Am. Chem. Soc.* 117:7029–7030, and in the related work presented in U.S. Pat. Nos. 5,525,734 and 5,525,735 and in International Patent Application WO 95/35278. All of these references disclose a method of synthesizing a combinatorial library of pyrrolidine compounds. Incorporation of the mercapto moiety is accomplished by coupling a mercapto acyl halide to the pyrrolidine nitrogen of the support-bound compounds.

A method of rapidly generating MMP inhibitors would find immediate application in generating lead compounds for pharmaceutical investigation. This invention provides methods for rapidly generating thiol compounds, which can then be subjected to high-throughput pharmacological screening for identification of compounds for further study.

All references, publications and patents mentioned herein are hereby incorporated by reference herein in their entirety.

DISCLOSURE OF THE INVENTION

The present invention provides methods for synthesizing combinatorial libraries of mercapto compounds and their derivatives on a solid support. The invention also encompasses the combinatorial libraries prepared by the synthetic methods of the invention. One method for synthesizing the mercapto compounds comprises adding one or more nucleophiles containing an S-protected mercapto group to a solid support wherein the solid support comprises a leaving group and an insoluble portion. The nucleophile displaces the leaving group on the solid support, producing an S-protected mercapto compound(s) bound to the insoluble portion. The solid support-bound mercapto compound(s) are derivatized by one or more chemical transformations, followed by deprotection of the mercapto group and cleavage of the compounds from the solid support. The deprotection of the mercapto group can be performed either before or after the cleavage of the compounds from the solid support.

In another method, a compound or compounds comprising a free mercapto group react with a solid support comprising a leaving group. The mercapto group replaces the leaving group on the solid support. The compound or compounds are then further derivatized, followed by cleavage of the compounds from the solid support.

In one embodiment, the methods are used to synthesize compounds and libraries of compounds of the formulas:

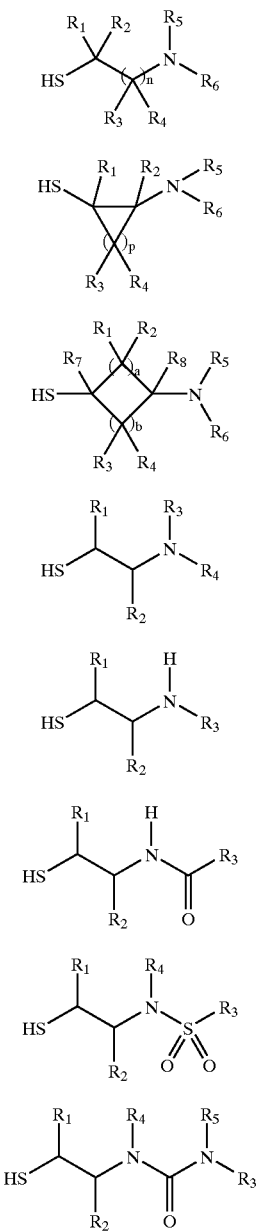

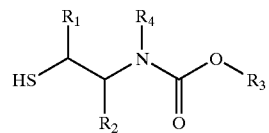

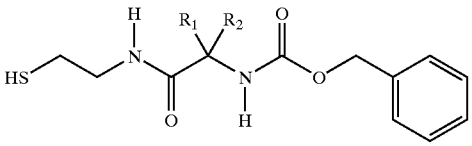

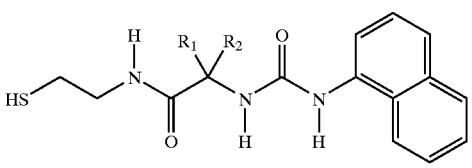

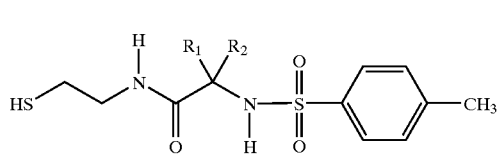

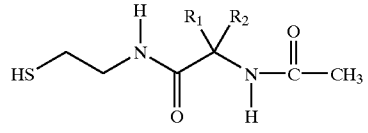

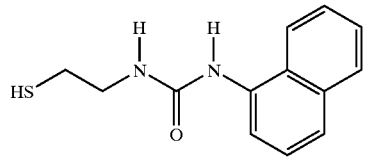

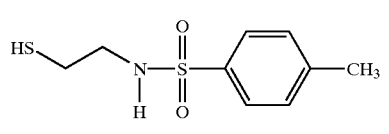

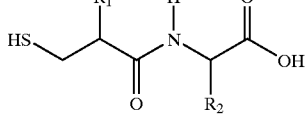

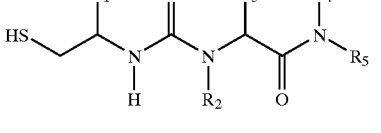

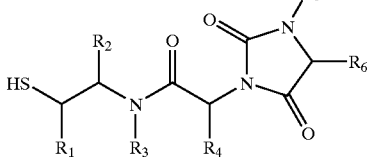

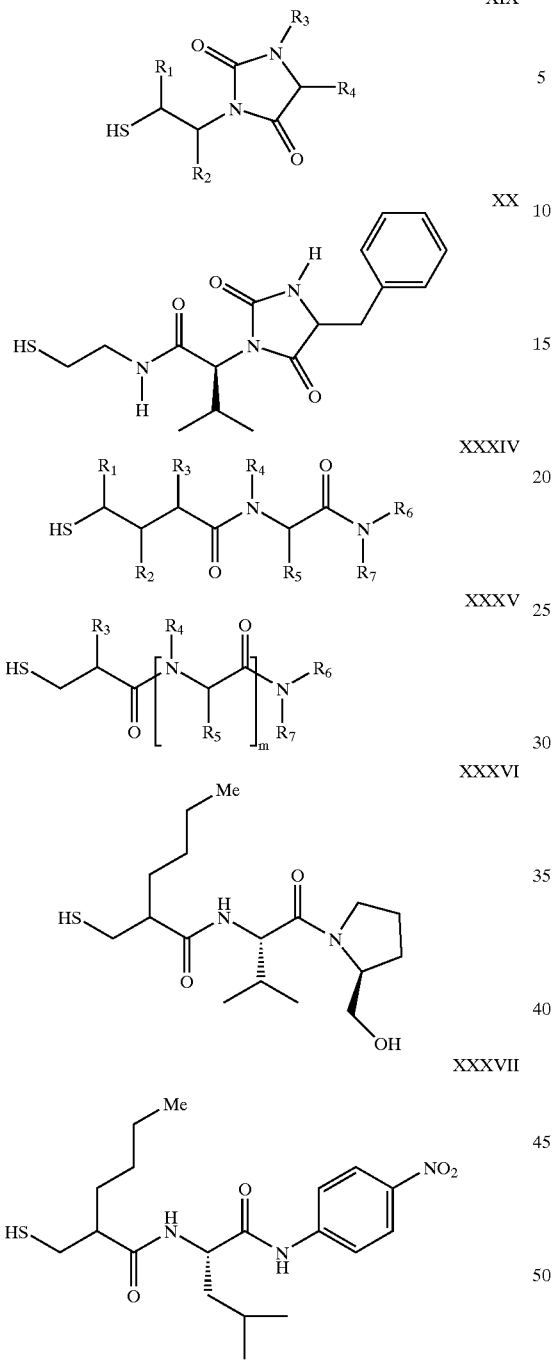

where one of $R_{50}$, $R_{51}$, $R_{52}$, $R_{53}$, and $R_{54}$ is —N($R_{55}$)($R_{56}$), —C(=O)—O—$R_{55}$, or —C(=O)—N($R_{55}$)($R_{56}$), and the remainder of $R_{50}$, $R_{51}$, $R_{52}$, $R_{53}$, and $R_{54}$, as well as $R_{55}$ and $R_{56}$, are independently selected from the group consisting of H, alkyl, heteroalkyl, aryl, heteroaryl, and heterocyclic moieties as defined herein, as well as amino acid side chains (both naturally and non-naturally occurring as defined herein). All stereoisomeric and diastereomeric variations of the compounds and substituents are included in the invention. All protected derivatives of the compounds and all salts of the compounds are also included in the invention.

In another embodiment, the invention encompasses methods of synthesizing a combinatorial library of mercapto compounds. In this embodiment, the nucleophile(s) is selected from the group consisting of compounds having the formula wherein $R_1$, $R_2$, $R_3$, $R_4$, $R_5$, and $R_6$ are independently selected from the group consisting of H, alkyl, heteroalkyl, aryl, heteroaryl, and heterocyclic moieties, and amino acid side chains; and where n is an integer from 1 to 5; p is an integer from 1 to 7; and a and b are independently integers from 1 to 8, with the proviso that (a+b)≦9.

In another embodiment, the invention encompasses further methods of synthesis of a combinatorial library of mercapto compounds. In this embodiment, the nucleophile (s) is selected from the group consisting of compounds having the formula wherein each of $R_1$, $R_2$, $R_3$, $R_4$, $R_5$, $R_6$, $R_7$, and $R_8$ are independently selected from the group consisting of H, alkyl, heteroalkyl, aryl, heteroaryl, and heterocyclic moieties as defined herein, as well as amino acid side chains (both naturally and non-naturally occurring as defined herein), and where n is an integer from 1 to 5, m is an integer from 0 to 5, p is an integer from 1 to 7, and a and b are integers ranging independently from 1 to 8 with the proviso that (a+b)≦9. The R groups can be attached to asymmetric carbon atoms in either the R-configuration or the S-configuration; additionally, all stereoisomeric and diastereomeric variations of the compounds and substituents are included in the invention.

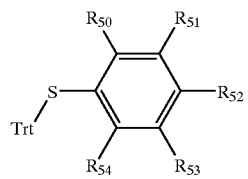

XXV where one of $R_{50}$, $R_{51}$, $R_{52}$, $R_{53}$, and $R_{54}$ is —NH$_2$, —COOH, or —C(=O)—NH$_2$, and the remainder of $R_{50}$, $R_{51}$, $R_{52}$, $R_{53}$, and $R_{54}$ are independently selected from the group consisting of H, alkyl, heteroalkyl, aryl, heteroaryl, and heterocyclic moieties and amino acid side chains.

In another embodiment, the invention also encompasses methods of synthesizing combinatorial libraries of mercapto compounds, where the nucleophile is S-trityl-2-aminoethanethiol.

In another embodiment, the invention also encompasses methods of synthesizing combinatorial libraries of mercapto compounds, where a mercaptoamine is added to a resin, with the mercapto group bound to the resin and the amino group is available for further reaction. In another embodiment, the resin is trityl alcohol resin and the mercaptoamine is 2-aminoethanethiol.

The invention also encompasses the combinatorial library or libraries of the compounds synthesized by the combinatorial method described above. These libraries are composed of a plurality of compounds from one or more classes of the compounds described above (formulas I–XVII and XVIII). Depending on the procedure used for synthesis, the combinatorial library preferably contains at least about 80, 160, 320, 640, 1000, 5000, 10,000, 50,000, 100,000, 500,000, 1,000,000, or more than 1,000,000 distinct compounds.

The invention also encompasses an S-protected mercapto compound functionalized resin, prepared by adding one or more nucleophile(s) comprising an S-protected mercapto group and a free nucleophilic amino group to a solid support.

The invention also encompasses linkers suitable for attachment to an amine-bearing resin, comprising an acid-labile linker group and an S-protected mercapto group.

The invention also encompasses the compounds represented by the formulas:

XXVI

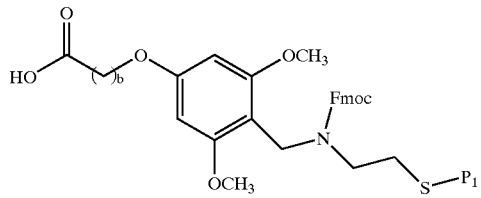

where b is an integer from 1 to 5 and $P_1$ is a protecting group selected from the group consisting of trityl, p-methoxytrityl, p-methyltrityl, acetamidomethyl, benzyl, t-butyl, t-butylthio, and p-methoxybenzyl protecting groups.

The invention also encompasses the compounds represented by the formulas:

XXVII

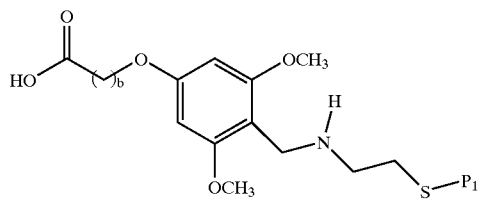

where b is an integer from 1 to 5 and $P_1$ is a protecting group selected from the group consisting of trityl, p-methoxytrityl, p-methyltrityl, acetamidomethyl, benzyl, t-butyl, t-butylthio, and p-methoxybenzyl protecting groups.

The invention also encompasses the compounds represented by the formulas:

XXVIII where b is an integer from 1 to 5; and where b is 3.

The invention also encompasses the compounds represented by the formulas:

XXIX where b is an integer from 1 to 5, and where b is 3.

The invention also encompasses the compounds represented by the formula

XXX

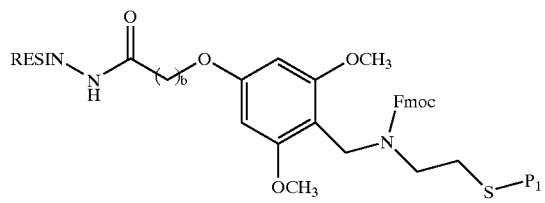

where b is an integer from 1 to 5, $P_1$ is a protecting group selected from the group consisting of trityl, p-methoxytrityl, p-methyltrityl, acetamidomethyl, benzyl, t-butyl, t-butylthio, and p-methoxybenzyl protecting groups, and RESIN is any solid or polymeric support.

The invention also encompasses the compounds represented by the formula

XXXI

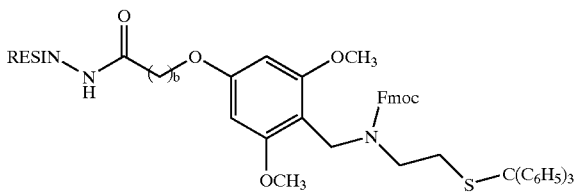

where b is an integer from 1 to 5, and RESIN is any solid or polymeric support.

The invention also encompasses the compounds represented by the formula

XXXII

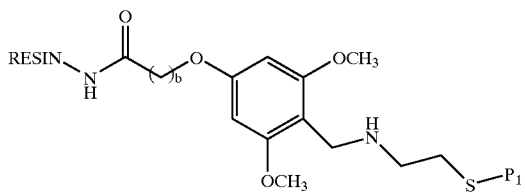

where b is an integer from 1 to 5, $P_1$ is a protecting group selected from the group consisting of trityl, p-methoxytrityl, p-methyltrityl, acetamidomethyl, benzyl, t-butyl, t-butylthio, and p-methoxybenzyl protecting groups, and RESIN is any solid or polymeric support.

The invention also encompasses the compounds represented by the formula

XXXIII

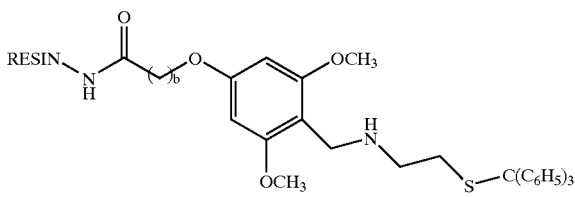

where b is an integer from 1 to 5, and RESIN is any solid or polymeric support.

The invention also encompasses the aforementioned compounds where RESIN-NH— is Tentagel S $NH_2$ resin in an amide linkage to the remainder of the compound, and/or where b is 3.

The invention also encompasses methods of use of the libraries obtained by the combinatorial methods. The uses include screening for bioactive compounds, by contacting the library with an enzyme, receptor, or cell under conditions conducive to specific binding, and isolating the mercapto compound or compounds that specifically bind to the enzyme, cell, or receptor.

The invention also encompasses methods of use of the libraries synthesized by the combinatorial methods to screen for pharmacologically active compounds. In one embodiment, the invention provides for a method for screening for inhibitors of the enzyme deformylase, by contacting the deformylase with a mercapto compound and determining the inhibition of the enzyme by the compound. In another embodiment, the invention provides a method for determining the antimicrobial efficacy of a compound, by screening compounds for their ability to inhibit deformylase, and then determining the antimicrobial activity of inhibitors of deformylase. In still another embodiment, the invention provides for compositions of matter which have antimicrobial activity or which inhibit a deformylase enzyme, and methods for inhibiting deformylase, affecting microbial growth, and treating microbial infections by administering the compositions of matter.

The invention also encompasses the bioactive compounds discovered by contacting the library with an enzyme, receptor, or cell under conditions conducive to specific binding, and isolating the mercapto compound or compounds that specifically bind to the enzyme, cell, or receptor. The invention also encompasses the bioactive compounds in combination with a pharmaceutically acceptable carrier.

The invention also encompasses use of the bioactive compounds in combination with a pharmaceutically acceptable carrier in treating diseases in mammals. Suitable diseases include, but are not limited to tumor growth, tumor invasion, tumor metastasis, angiogenesis during cancer development, abdominal aortic aneurysms, inflammation, arthritis, and hemorrhagic brain injury.

BEST MODE FOR CARRYING OUT THE INVENTION

Definitions

Figure 1:
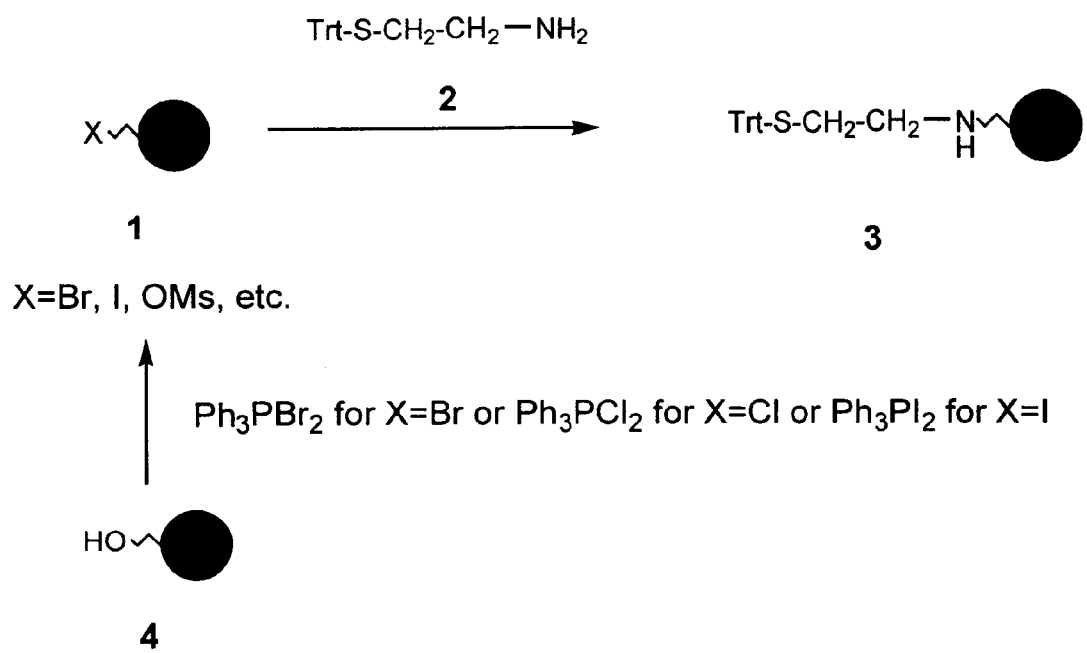
FIG. 1 illustrates a synthetic route to a resin suitable for the method of synthesis described herein.

The term "bioactive molecule," as used herein, refers to a molecule that has inhibitory activity. "Inhibitory activity" can be determined by inhibition of the interaction between a target and its respective substrate(s) or endogenous ligand (s). Target molecules include, but are not limited to, enzymes and receptors. Typically, inhibition is reduced by at least about 15% compared to the interaction of the target and substrate in the absence of the bioactive molecule, where the bioactive molecule is at a solution concentration of $10^{-3}$ molar or lower. Inhibitory activity can also be determined by exhibition of a dissociation constant of about $10^{-3}$ of the bioactive molecule with other biological macromolecules, such as DNA, RNA, polysaccharides and proteins not previously included as enzymes or receptors. Preferably, the bioactive molecule has a dissociation constant of about $10^{-4}$ molar or less. More preferably, the molecule has a dissociation constant of about $10^{-5}$ molar or less. Most preferably, the molecule has a dissociation constant of about $10^{-6}$ molar or less. These macromolecules can include, but are not limited to, macromolecules derived from prokaryotic or eukaryotic sources.

"Chemical library" or "array" is an intentionally created collection of differing molecules which can be prepared synthetically. In the present invention, the library can be screened for biological activity in a variety of different formats (e.g., libraries of soluble molecules, libraries of molecules bound to a solid support).

"Alkyl" refers to a cyclic, branched, or straight chain chemical group containing carbon and hydrogen, such as methyl, pentyl, and adamantyl. Alkyl groups can either be unsubstituted or substituted with one or more substituents, e.g., halogen, alkoxy, acyloxy, amino, hydroxyl, mercapto, carboxy, benzyloxy, phenyl, benzyl, nitro, or other functionality that can be suitably blocked, if necessary for purposes of the invention, with a protecting group. Alkyl groups can be saturated or unsaturated (e.g., containing —C=C— or —C≡C— subunits), at one or several positions. "Heteroalkyl" groups encompass alkyl chains with one or more N, O, S, or P heteroatoms incorporated into the chain, with the heteroatom bearing none, one, or more than one of the substituents described above, as well as oxidized forms of the heteroatoms N, S and P. Unless specified otherwise, the alkyl groups described herein preferably comprise about 1 to 12 carbon atoms, more preferably 1 to 10, and most preferably 1 to 8 carbon atoms. Unless specified otherwise, heteroalkyl groups preferably comprise about 1 to 12 carbon atoms in addition to any heteroatom(s) present in the chain, more preferably 1 to 10 carbon atoms in addition to any heteroatom(s) present in the chain, and most preferably 1 to 8 carbon atoms in addition to any heteroatom(s) present in the chain.

"Mercapto" is used synonymously with "thiol." Mercapto group and thiol group are thus used to indicate the —SH group, and mercapto compound and thiol compound are thus used to indicate a compound containing an —SH group. When a compound containing a mercapto group carries a protecting group on the —SH group, that is, the mercapto group is protected as —S-Prot, where Prot is the protecting group, the compound can still referred to as a mercapto compound as the protecting group can be easily removed, regenerating the —SH group. Typically such a compound is referred to as a "protected mercapto compound." Similarly, when a compound containing a mercapto group is attached to a solid support, such as a resin, by the mercapto group, i.e., —S-RESIN, the compound can still be referred to as a mercapto compound, as the —SH group is regenerated upon cleavage from the resin. Typically such a compound is referred to as a "resin-bound mercapto compound."

"Amino acid" refers to any of the naturally occurring amino acids, as well as optical isomers (enantiomers and diastereomers), synthetic analogs and derivatives thereof. α-Amino acids comprise a carbon atom to which is bonded an amino group, a carboxyl group, a hydrogen atom, and a distinctive group referred to as a "side chain." α-Amino acids also comprise a carbon atom to which is bonded an amino group, a carboxyl group, and two distinctive groups (which can be the same group or can be different groups), in which case the amino acid has two side chains. The side chains of naturally occurring amino acids are well known in the art and include, for example, hydrogen (e.g., as in glycine), alkyl (e.g., as in alanine, valine, leucine, isoleucine), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), and heteroarylalkyl (e.g., as in histidine and tryptophan). See, e.g., Harper et al. (1977) *Review of Physiological Chemistry,* 16th Ed., Lange Medical Publications, pp. 21–24. One of skill in the art will appreciate that the term "amino acid" also includes β- γ-, δ-, and ω-amino acids, and the like, and α-imino acids such as proline. As used herein, "amino acids" includes proline. Non-naturally occurring amino acids are also known in the art, as set forth in, for example, Williams (ed.), *Synthesis of Optically Active α-Amino Acids,* Pergamon Press, 1989; Evans et al. (1990) *J. Amer. Chem. Soc.,* 112:4011–4030; Pu et al. (1991) *J. Amer. Chem. Soc.* 56:1280–1283; and Williams et al. (1991) *J. Amer. Chem. Soc.* 113:9276–9286; and all references cited therein.

"Aryl" or "Ar" refers to a monovalent unsaturated aromatic carbocyclic group having a single-ring (e.g., phenyl, anilino) or multiple condensed rings (e.g., naphthyl or anthryl), which are optionally unsubstituted or substituted with amino, hydroxyl, $C_{1-8}$ alkyl, $C_{1-8}$ heteroalkyl, alkoxy, chloro, halo, mercapto, nitro and other substituents (e.g. p-nitroanilino, 2-hydroxynaphthyl).

"Electron withdrawing group" refers to a substituent that attracts electrons to itself more than a hydrogen atom would if it occupied the same position in a molecule. Examples of electron withdrawing groups include, but are not limited to, —$NR_2$, —COOH, —OR, —$SR_2$, —F, —Cl, —Br, —COR, —SH, $NO_2$, —SR, —$SO_2R$, —I, —OH, —CN, —CH=CHR, —COOR, —Ar, —CH=$CR_2$, where R is alkyl, aryl, arylalkyl, or heteroaryl. Any group mentioned herein may be substituted with zero, one or more of these electron withdrawing groups (although substitutions are not limited to these groups) at any point where substitution is permitted.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within at least one of the rings. The ring(s) can optionally be unsubstituted or substituted with substituents including, but not limited to, amino, hydroxyl, $C_{1-8}$ alkyl, $C_{1-8}$ heteroalkyl, alkoxy, halo, and mercapto, and nitro.

"Protecting group" refers to a chemical group that exhibits at least one of the following characteristics: 1) reacts selectively with the desired functionality in good yield to give a protected substrate that is stable to the reactions for which protection is desired; 2) is selectively removable from the protected substrate to yield the desired functionality; and 3) is removable in good yield by reagents compatible with the other functional group(s) generated in such projected reactions. Examples of suitable protecting groups can be found in Greene et al. *Protective Groups in Organic Synthesis,* 2nd Ed., John Wiley & Sons, Inc., New York, 1991. Preferred thiol protecting groups include, but are not limited to, trityl (Trt), p-methoxytrityl (Mmt), p-methyltrityl (Mtt), acetamidomethyl (Acm), benzyl (Bzl), t-butyl (tBu), t-butylthio (tButhio), and p-methoxybenzyl (pMeOBzl). Preferred terminal amino protecting groups include benzyloxycarbonyl (CBz), t-butyloxycarbonyl (Boc), t-butyldimethylsilyl (TBDIMS), 9-fluorenylmethoxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include t-butyl, TBDIMS, photolabile protecting groups (such as nitroveratryl oxymethyl ether (Nvom)), Mom (methoxy methyl ether), and Mem (methoxy ethoxy methyl ether). A particularly preferred protecting group for thiols is trityl (Trt). "Protected derivative" of a compound is used to refer to a compound which has been protected with a protecting group, such as those described above.

The phrase "distinct compound" is used to refer to compounds which are chemically different, except that salts of a compound are not considered distinct from the corresponding compound from which the salt is derived. Thus, L-valine and D-valine are defined herein as two distinct compounds, whereas L-valine and L-valine hydrochloride salt are not defined herein as two distinct compounds.

The phrase "free nucleophilic amino group" is used to refer to an amino group on a molecule which is available as the nucleophile in nucleophilic addition reactions.

Abbreviations

The following abbreviations are used:
AcOH, HOAc=acetic acid
$Ac_2O$=acetic anhydride
DBU=1,8-diazabicyclo[5.4.0]undec-7-ene
DCM=dichloromethane
DIC=diisopropylcarbodiimide
DIAD=diisopropylazodicarboxylate
DIEA=diisopropylethylamine
DMAP=4-dimethylaminopyridine
DMF=dimethylformamide
EtOAc=ethyl acetate
HATU =O-(7-aza-benzotriazol-1-yl)-N,N,N',N'-tetramethyluronium hexafluorophosphate
MeOH=methanol
MIC=minimum inhibitory concentration
MMP=matrix metalloproteinase
NMM=N-methyl morpholine
Py=pyridine
PyBOP=benzotriazole-1-yl-oxy-tris-pyrrolidino-phosphonium hexafluorophosphate
RT=room temperature
TBP=tributylphosphate
TES=triethylsilane
TFA=trifluoroacetic acid
TFAPfp=pentafluorophenyl trifluoroacetate
TGS resin=Tentagel S resin
THF=tetrahydrofuran
TMAD=N,N,N',N'-tetramethylazodicarboxamide (1,1'-Azobis(N,N-dimethylformamide))
TMOF=trimethylorthoformate
TPP=triphenyl phosphine
TsCl=tosyl chloride
Trt=trityl

Resins

A solid phase support suitable for preparing combinatorial libraries of mercapto derivative compounds must anchor the synthetic intermediates stably during the chemical steps required to assemble the compounds on the support. Once the synthesis of the compounds is completed, they must be capable of being cleaved from the support under conditions which do not have a deleterious effect on the compounds. Solid phase supports which meet these criteria have been developed; see Ngu and Patel(1997) *Tet. Lett.* 38:973. The supports are derived from Wang resin (Wang (1973) *J. Am. Chem. Soc.* 95:1328) and Tentagel S AC resin (Florsheimer et al. *Peptides* 1990: *Proceedings of the 21st European Peptide Symposium* (Giralt and Andreu, eds.); Leiden: Escom, 1991, p. 131; available from Rapp Polymere, Tubingen, Germany).

FIG. 1 shows various methods of preparing resins, and subsequently immobilizing a mercapto derivative onto the resin. In FIG. 1, a starting resin 4 (Wang or Tentagel S AC resin) is functionalized to replace the active hydroxyl group with a leaving group X, where X can be bromine or iodine (see Table 1 below). This functionalized resin 1 can then be reacted with a mercaptoamine of the form 2 (where $R_1$ is an alkyl group as defined herein) to form a mercaptoamine resin 3, which can be further derivatized. Brominated Tentagel S AC resin is an example of a resin which can be used for synthesis of the mercapto compounds. The concentration of TFA required to cleave compounds from the derivatized Tentagel S AC resin will vary according to the compounds synthesized. The resins used, and a general scheme for preparing derivatized resins used in the invention, are as follows:

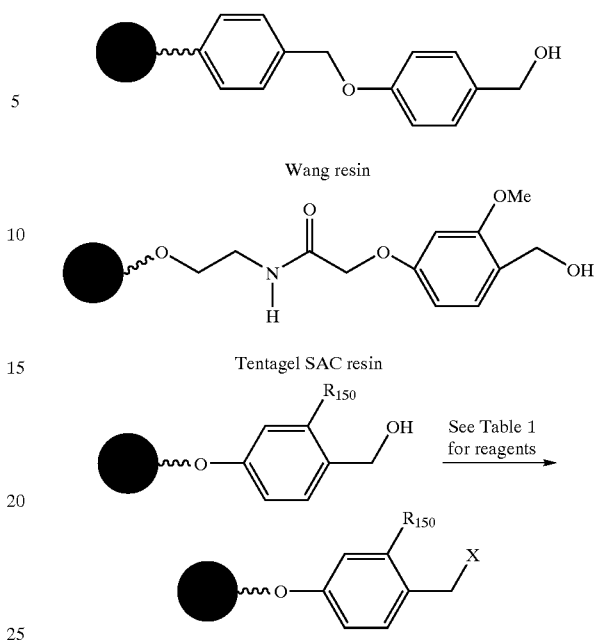

$R_{150}$=H (Wang resin)
$R_{150}$=OMe (Tentagel S AC resin)
(in addition, linker to polymer backbone differs between the two resins)

As shown herein, conversion of the original Wang or Tentagel S AC resin to the derivatized form was assayed by reacting n-butylamine with the derivatized resin, then washing away unreacted amine. The resin was then reacted with 2-naphthalenesulfonyl chloride. Resins on which the X group was displaced by nucleophilic attack of the amine yielded n-butyl-(2-naphthyl)-sulfonamide upon cleavage of the resin with trifluoroacetic acid. Resins not converted to the derivatized form, or unstable after conversion and reverted back to the original resin, yielded 2-naphthalenesulfonic acid upon cleavage. The yield of sulfonylated amine (and hence of stable derivatized resin in the scheme depicted above) is summarized in Table 1, along with the reagents used for the derivatization of the resins.

TABLE 1

Reagents for Derivatizing Wang and Tentagel S AC Resins

| Reagents | X (leaving group on modified resin) | Yield of Derivatized Amine from Modified Wang resin | Yield of Derivatized Amine from Modified Tentagel S AC resin |
|---|---|---|---|
| $Ph_3PBr_2$ or $Ph_3P/CBr_4$ | Br | 99% | 87% |
| $Ph_3PI_2$ or $Ph_3P/$ diisopropyl azodicarboxylate/ $CH_3I$ | I | 93% | 79% |
| methanesulfonyl chloride/ N-methyl morpholine | mesyl | 95% | not assayed |
| toluenesulfonyl chloride/ N-methyl morpholine | tosyl | 0% | not assayed |
| 4-nitrobenzenesulfonyl chloride/ N-methyl morpholine | nosyl | 0% | not assayed |

An alternative route to producing a resin suitable for combinatorial synthesis is provided by coupling an S-protected mercapto compound to a linker in solution, and attaching the S-protected mercapto compound-linker to an appropriate resin. The scheme below illustrates the attachment of a linker (Sharma et al. (1993) *J. Org. Chem.* 58:4993; Albericio et al. (1991) *Tet. Lett.* 32:1015; and Albericio et al. (1990) *J. Org. Chem.* 55:3730) to the S-protected mercapto compound $NH_2$—$CH_2$—$CH_2$—S—Trt, where Trt is the trityl protecting group. Examples of other S-protected mercapto compounds include, but are not limited to, $NH_2$—$CH_2$—$CH_2$—S—Mtt, $NH_2$—$CH_2$—$CH_2$—S—Mmt, $NH_2$—$CH_2$—$(C_6H_4)$—$CH_2$—S—Trt other compounds, utilizing protecting groups compatible with the chemical steps used in the synthesis. The specific example depicted below, using a trityl protected compound, is intended to illustrate the invention, and does not limit the invention in any manner.

Schemes for Coupling a Linking Group to an S-Protected Mercapto Compound

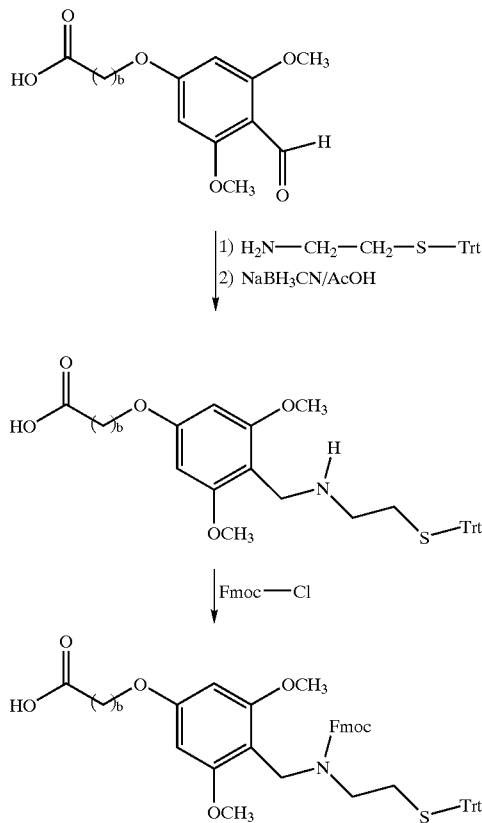

where b is an integer from 1 to 5.

The N-protected, S-protected mercapto compound-linker intermediate can then be coupled to any of a variety of amine resins and used for solid-phase combinatorial synthesis.

The following scheme exemplifies a method of coupling of the N-Fmoc protected, S-protected mercapto compound-linker to the resin, using trityl as the protecting group as indicated above:

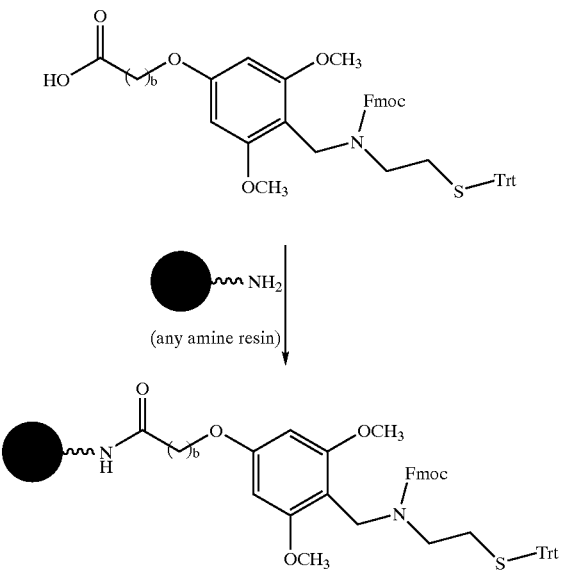

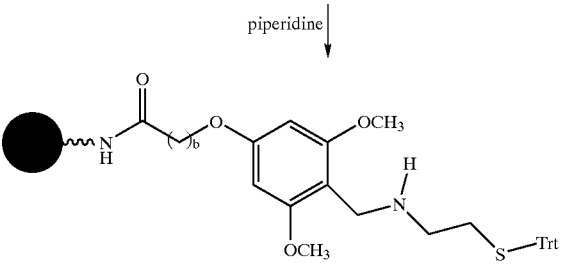

where b is an integer from 1 to 5.

Examples of amine resins to which the N—Fmoc protected, S-protected mercapto compound-linker intermediate can be coupled include, but are not limited to, Tentagel S $NH_2$ resin, benzhydrylamine and p-methylbenzhydrylamine resins, aminomethylated polystyrene resin, and other resins bearing an amine group.

Alternatively, the linker can be first coupled to the resin, and the S-protected mercapto compound can then be coupled to the resin. For synthesis using S-protected mercaptoamines, this method is convenient in that it eliminates the need for temporary Fmoc protection of the amine function. This method is illustrated below using $H_2N$—$CH_2$—$CH_2$—S—Trt:

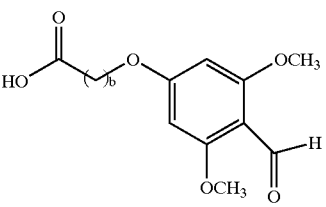

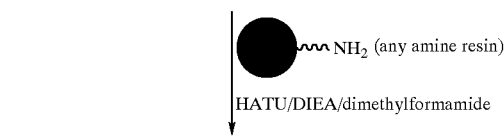

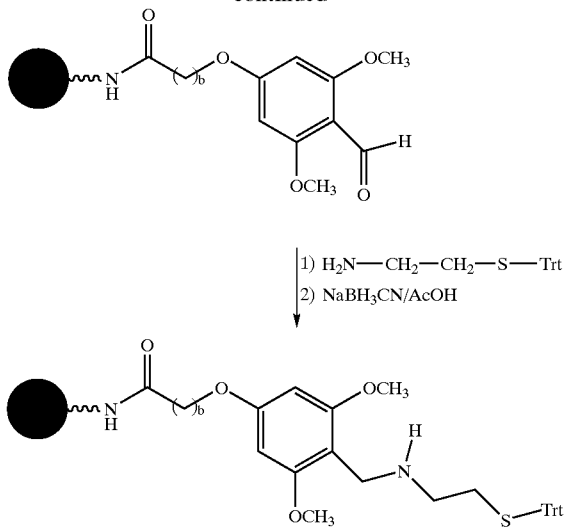

where b is an integer from 1 to 5.

Alternate Scheme for Linking a Mercaptoamine to a Resin

Yet another means of synthesizing combinatorial libraries of mercapto compounds involves direct attachment of the thiol group to a suitable resin. One such example is illustrated below:

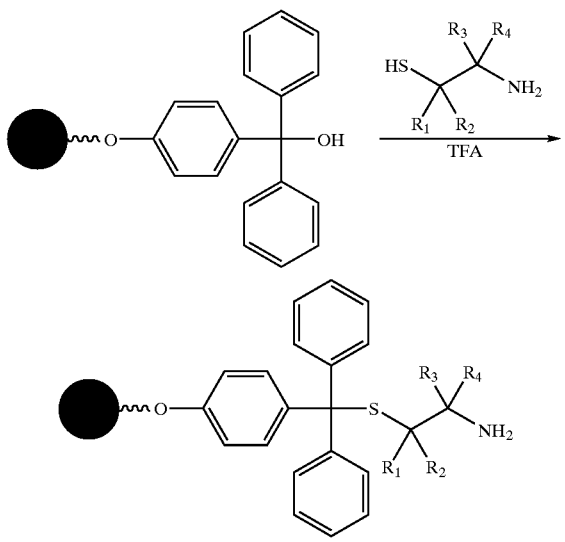

where each of $R_1$, $R_2$, $R_3$, and $R_4$ are independently selected from the group consisting of H, alkyl, heteroalkyl, aryl, heteroaryl, and heterocyclic moieties, and amino acid side chains. The unprotected amine can then be derivatized using a variety of chemical transformations to yield the desired combinatorial libraries.

The general structures described above can take a wide variety of forms; substitution of various groups at any of the variable positions yields a wide variety of compounds. The power of combinatorial synthesis is readily exploited by introducing a mixture of reagents at each step where a variable substituent is possible in the structure. For example, if an N-alkylated mercaptoamine is desired, an immobilized, S-protected mercaptoamine on the resin can be reacted with a mixture of alkyl chlorides (for example butyl chloride, 2-chloropropane, and benzyl chloride). The reagents can be provided in concentrations inversely proportional to their rates of reaction with the immobilized intermediate, so that approximately equal amounts of the various components of the combinatorial mixture are produced. The reaction rates can be assayed by techniques well known in the art. One such assay involves introducing a single substituent at each of the variable steps, except at the step where coupling rates are to be assayed. At that step, an equimolar mixture of the various reagents which introduce the varied substituents is provided. The intermediates produced after that step are cleaved from the resin, and separated and analyzed on a GC/MS or LC/MS apparatus, or using other appropriate analytical instruments or methods. This yields information about the relative coupling rates of the reagents used. This method is a generalization of the method for assaying reaction rates of reagents for introducing amino acids in peptide synthesis, provided by Rutter et al. in U.S. Pat. No. 5,010,175.

Instead of mixing several reagents at one step as described above, combinatorial libraries can also be prepared by using the "split and pool" protocol described by Furka et al. (1991) *Int. J. Pept. Prot. Res.* 37:487. In this method, the total number of reactions grows in an additive fashion with the number of steps, but the number of compounds prepared grows in a multiplicative fashion.

Finally, a combinatorial library can also be prepared by performing parallel synthesis, where compounds are prepared in parallel as discrete compounds or as small pools of compounds.

All of these methods for generating combinatorial libraries of compounds can be performed by automated, semi-automated, or manual protocols and techniques, according to methods well known in the art.

Cleavage of Compounds from the Resin

Cleavage of the compounds from the derivatized resins such as Wang or Tentagel S AC resins is accomplished under acidic conditions. Preferably, 95–100% TFA is used to cleave compounds attached to the Wang resin. A small portion (typically 5% or less) of the cleavage solution can be composed of scavenger compounds, the purpose of which is to trap carbocations released during the cleavage process to prevent the cations from reacting with the desired products. The chemical composition of the products and their sensitivity to alkylation by carbocations will determine the appropriate scavenger or scavengers. Such scavenger compounds are well-known in the field of peptide synthesis and include substances such as thiols (e.g. 1,2-ethanedithiol), phenols, trialkylsilyl compounds, anisole, thioanisole, water, and sulfides (e.g., methyl ethyl sulfide). In appropriate cases it is desirable to reduce the amount of TFA below 95% and increase the proportion of scavengers used accordingly.

The compounds of the present invention can also be synthesized on derivatized Tentagel S AC resins. In cleaving compounds from Tentagel S AC-derived resins, typically a solution ranging from 5–50% trifluoroacetic acid in DCM is used, with the optional addition of scavengers such as those indicated above. However, if the nitrogen of an amide or sulfonamide is the attachment point to the resin, as in, for example, the nitrogen of the resin-bound compound below:

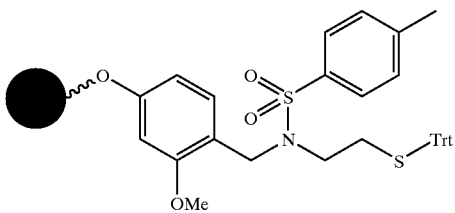

then cleavage of the compound from the resin will require a higher concentration of TFA. For such compounds of this invention, 95% TFA is typically used. The trityl group of the resin-bound compound depicted immediately above can be selectively removed with 6% TFA/6% TES solution in DCM, yielding a free thiol group with the compound still attached to the resin.

Screening

The present invention is directed toward the generation of libraries of mercapto derivatives. These libraries are used to select one or more mercapto derivative species that demonstrate a specific interaction with a target. A target is selected when it is believed to be of importance in the modulation of a disease. Examples of disease states for which mercapto derivative libraries can be screened include, but are not limited to, tumor growth, tumor invasion, tumor metastasis, angiogenesis during cancer development, abdominal aortic aneurysms, inflammation, arthritis, hemorrhagic brain injury, connective tissue disorders, and retinopathies.

Several methods have been developed in recent years to screen libraries of compounds to identify the compounds having the desired characteristics for interacting with a target. Targets include, but are not limited to, enzymes and receptors. When a compound inhibits the interaction between a target and its respective substrate(s) or endogenous ligand(s), by at least 15%, at a solution concentration of $10^{-3}$ molar or lower (i.e., it has inhibitory activity), or it exhibits a dissociation constant of $10^{-3}$ or lower with other biological macromolecules, such as DNA, RNA, polysaccharides and proteins not previously included as enzymes or receptors, the compound is thought to demonstrate a specific interaction with the target. Methods for isolating library compound species that demonstrate desirable affinity for a target, including, but not limited to, a receptor or enzyme, are well-known in the art.

For example, an enzyme solution can be mixed with a solution of the compounds of a particular combinatorial library under conditions favorable to enzyme-ligand binding. See Bush et al. (1993) *Antimicrobial Agents and Chemotherapy* 37:851–858; and Daub et al. (1989) *Biochemistry* 27:3701–3708. Specific binding of library compounds to the enzyme can be detected by any of the numerous enzyme inhibition assays which are well known in the art. Compounds bound to the enzyme can be readily separated from compounds which remain free in solution by applying the solution to a column such as a Sephadex G-25 gel filtration column. Free enzyme and enzyme-ligand complex pass through the column quickly, while free library compounds are retarded in their progress through the column. The mixture of enzyme-ligand complex and free enzyme are then treated with a powerful denaturing agent, such as guanidinium hydrochloride or urea, to cause release of the ligand from the enzyme. The solution is injected onto an HPLC column, for example, a Vydac C-4 reverse-phase column, eluted with a gradient of water and acetonitrile ranging from 0% acetonitrile to 80% acetonitrile. Diode array detection provides discrimination of the compounds of the combinatorial library from the enzyme. The compound peaks are then collected and subjected to mass spectrometry for identification.

An alternate manner of identifying compounds that inhibit an enzyme is to divide the library into separate sublibraries where one step in the synthesis is unique to each sublibrary. To generate a combinatorial library, reactants are mixed together during a step to generate a wide mixture of compounds. At a certain step in the synthesis, however, the resin bearing the synthetic intermediates can be divided into several portions, with each portion then undergoing a unique transformation. The resin portions are then (separately) subjected to the rest of the synthetic steps in the combinatorial synthetic method. Each individual resin portion thus constitutes a separate sublibrary. When testing the compounds, if a given sublibrary shows more activity than the other sublibraries, the unique step of that sublibrary is held fixed. The sublibrary then becomes the new library, with that step fixed, and forms the basis for another round of sublibrary synthesis, where a different step in the synthesis is optimized. This procedure can be executed at each step until a final compound is arrived at. The aforementioned method is the generalization of the method described in Geysen, WO 86/00991, for determining peptide "mimotopes," applied to the synthetic method of this invention.

Finding a compound that inhibits an enzyme is most readily performed with free compound in solution. However, the compounds can also be screened while still bound to the resin used for synthesis. For certain targets and in some applications, this is the preferable mode of finding compounds with the desired characteristics. For example, the compounds can be synthesized using resin beads for a solid support. If a compound which binds to a specific antibody is desired, the resin-bound library of compounds can be contacted with an antibody solution under conditions favoring a stable antibody-compound-resin complex. A fluorescently labeled second antibody which binds to the constant region of the first antibody can then be contacted with the antibody-compound-resin complex, again under favorable binding conditions. This will allow identification of a specific bead as carrying the compound which is recognized by the first antibody binding site. The bead can then be physically removed from the resin mixture and subjected to analysis. If the synthesis has been conducted in a manner such that only one compound is likely to be synthesized on a particular bead, then the binding compound has been identified. If the synthesis has been carried out so that many compounds are present on a single bead, the information derived from analysis can be utilized to narrow the synthetic choices for the next round of synthesis and identification.

The enzyme, antibody, receptor, or other target need not be in solution. Antibody or enzyme can be immobilized on a column. The library of compounds can then be passed over the column, resulting in the retention of strongly binding compounds on the column after weaker-binding and non-binding compounds are washed away. The column can then be washed under conditions that dissociate protein-ligand binding, which will remove the compounds retained in the initial step. These compounds can then be analyzed, and synthesized separately in quantity for further testing. Similarly, cells expressing cell surface receptors can be contacted with a solution of library compounds. The cells bearing bound compounds can be readily separated from the solution containing non-binding compounds (e.g., by centrifugation). The cells can then be washed with a solution which will dissociate the bound ligand from the cell surface receptor. Again, the cells can be separated from the solution, and the solution which now contains the ligands bound in the initial step can be analyzed.

Assays appropriate for measuring the inhibition or modulation of the activity of biological molecules (such as enzymes) by the compounds of the invention can be found in the following publications: *Methods in Enzymology* Vol. 248, *Proteolytic Enzymes: Aspartic and Metallo Peptidases*, (Alan J. Barrett, ed.), New York: Academic Press, 1995, Chapters 1–6 and 13–51; *Methods in Enzymology* Vol. 80, New York: Academic Press, 1981, Chapters 52 and 53; Cawston et al. (1981) *Biochem. J.* 195: 159–165; Sellers et al. (1977) *Biochem. J.* 167:353; Sellers et al. (1978) *Biochem. J.* 171: 493–496; Sellars et al. (1977) *Biochem J.* 163:303; Murphy et al. (1977) *Bioch. Biophys. Acta* 483:493; and Cawston et al. (1979) *Anal. Biochem.* 99: 340–345. Some of the publications mentioned in the Background Art section above also contain information regarding assays that can be used to determine the effects which the compounds of the invention have on biological molecules.

Metalloenzyme Inhibitors

The mercapto compound libraries of the present invention are used to select one or more mercapto compound species that exhibit a specific interaction with a target. Included among the targets are enzymes, particularly metalloenzymes, more particularly metallopeptidases. Metallopeptidases as targets can be from a variety of sources, including plants, animals, eubacteria, fungi, protozoans, and archaebacteria. Metallopeptidase targets include, but are not limited to, bacterial metallopeptidases; fungal metallopeptidases; snake venom metalloendopeptidases (Jia et al. (1996) *Toxicon* 34:1269–1276); and eukaryotic matrix metalloproteinases. The bacterial metallopeptidases include, but are not limited to, thermolysins and serrolysins (see Kooi and Sokol (1996) *J. Med. Microbiol.* 45:219–225); tetanus and botulism neurotoxins; and peptide deformylase (Chan et al. (1997) *Biochem.* 36:13904–13909). Matrix metalloproteinases include, but are not limited to, collagenase-1, -2, and -3, stromelysin-1, -2, and 3, gelatinase A, gelatinase B, matrilysin, macrophage elastase, and MT-MMP's.

To identify inhibitors of metalloproteinases, the enzyme used can be native enzyme, i.e., enzyme as isolated from a natural source, or can be a fusion protein, a fragment, or a mimetope, as long as the peptidase function of the protein is intact. The term "metalloproteinase", as used herein, encompasses a metalloproteinase isolated from a natural source; a fusion protein comprising a metalloproteinase; or a mimetope; or a portion of any of the foregoing, as long as the metalloproteinase retains peptidase activity. A fusion protein comprising a metalloproteinase includes a metalloproteinase domain attached to a fusion segment. The fusion segment can serve to enhance the protein's stability during production, storage, and/or use. The fusion segment can also serve to simplify purification of the fusion protein, for example, by affinity chromatography based on capture of the fusion segment. Examples include, but are not limited to, an immunoglobulin binding segment such as protein A, protein G or Fc receptor, or portions thereof; a tag domain which is recognized by an antibody; and a metal binding domain, such as a poly-histidine segment which binds divalent cations. A mimetope of a protein includes any compound that mimics the activity of that protein. Mimetopes include, but are not limited to, antiidiotypic and/or catalytic antibodies, or fragments thereof.

The source of the enzyme target can be any known source, including, for example, natural sources such as bacterial, mammalian, fungal, or plant cells; enzyme made using recombinant DNA technology; or enzyme produced by chemical synthesis. Many metalloproteinases can be obtained from commercial sources. For bacterial metalloproteinases, metalloproteinases can be obtained from culture supernatant, or, alternatively, cells can be disrupted, for example, by high pressure or sonication. Methods of obtaining metalloenzymes from mammalian cells are known in the art. For example, MMPs can be at least partially purified from isolated leukocytes by homogenizing the leukocytes in detergent to disrupt the cell membrane, and subjecting the homogenate to ion-exchange column chromatography, then affinity chromatography comprising extracellular matrix components, as described. Okamoto et al. (1997) *J. Biol. Chem.* 272:6059–6066.

The metalloproteinase can be produced by recombinant DNA technology. Techniques for preparing polynucleotide constructs for expression of a protein in a bacterial, insect, mammalian, yeast, or plant cell are known in the art and can be found in a variety of sources, including *Current Protocols in Molecular Biology*, eds. Ausubel et al., Greene Publishing and Wiley-Interscience: New York (1987) and periodic updates. For example, a polynucleotide sequence encoding a metalloproteinase is operably linked to control sequences for transcription and translation. A control sequence is "operably linked" to a coding sequence if the control sequence regulates transcription or translation. Any method in the art can be used for the transformation, or insertion, of an exogenous polynucleotide into a host cell, for example, lipofection, transduction, infection or electroporation, using either purified DNA, viral vectors, or DNA or RNA viruses. The exogenous polynucleotide may be maintained as a non-integrated vector, for example, a plasmid, or alternatively, may be integrated into the host cell genome. Those skilled in the art will recognize that additional sequences which confer increased stability, and/or which facilitate isolation of, the synthesized metalloproteinase can be included in a construct.

Methods for chemical synthesis of proteins are known in the art and can be used to produce metalloproteinases.

The activity of the metalloproteinase, as well as inhibition of activity, can be measured using any known method. For metalloproteinases which act to activate a proenzyme, assay methods include activation of a proenzyme, and measurement of activated proenzyme activity. Such a method would comprise the steps of incubating the metalloproteinase with the proenzyme for a time sufficient to result in substantial conversion of the proenzyme substrate into activated enzyme; adding a substrate for the activated enzyme; and determining the amount of product of the activated enzyme's activity on the substrate. For example, if the proenzyme is a trypsin-like enzyme, then activity of the metalloproteinase can be measured as released trypsin activity from a pro-trypsin-like protease, using as the substrate for the trypsin activity paranitrophenol derivatized substrates for trypsin. Alternatively, if the proenzyme is an MMP, then any of the known assays for MMPs can be used.

Metalloproteinase activity can also be measured directly, using, for example, an azocasein assay. (Long et al. (1981) *J. Gen. Microbiol.* 127:193–199). The assays can be spectrophotometric, fluorimetric, radioactive, or luminometric, depending upon the choice of substrate. For example, fluorimetric assays for MMP activity can employ FITC-labeled collagen, as described. Baici et al. (1980) *Anal. Biochem.* 108:230–232. Methods of measuring peptide deformylase activity are provided in Example 22.

If desired, comparison of the inhibitory activity of an inhibitor of the present invention with known inhibitors of metalloproteinases can be made. Known inhibitors of metalloproteinases include metal chelators such as o-phenanthroline, ethylene diaminetetraacetic acid (EDTA), and ethylene glycol bis(beta-amino-ethylether) N,N,N',N'-tetraacetic acid (EGTA).

Pharmacological Applications

Those compounds selected as having pharmacological activity can be useful as drugs for the treatment of disease states in mammals, including humans. Such drugs comprise compounds of the invention in amounts and formulations appropriate for therapeutic effect in any of the diseases amenable to such treatment. The drugs also comprise any pharmaceutically acceptable salt of the compounds, as well as any carrier or excipient appropriate for the drug. Carriers and excipients well known in the art can be used, such as those disclosed in *Remington's Pharmaceutical Sciences*, Mack Publishing Company, Easton, Pa. The compounds of the invention, or salts thereof, can be formulated in such a manner as to be administered in any suitable format including, but not limited to, orally; nasally; parenterally (e.g. intravenously and intramuscularly, as a solution); in medicaments for rectal or vaginal application; in medicaments for application to the skin and mucous membranes (e.g. as solutions, lotions, emulsions, patches, salves, plasters, etc.); and in medicaments for topical application to the eyes. The compounds can also be administered in liposome formulations. The compounds can also be administered as prodrugs, where the prodrug administered undergoes biotransformation in the treated mammal to a form which is biologically active.

The following examples are provided as illustrations of the methods described, and are not intended to limit the invention in any way.

EXAMPLES
Example 1

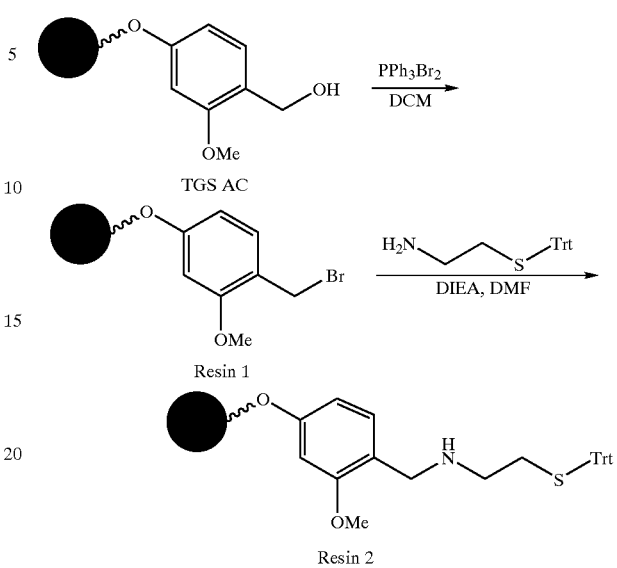

Preparation of Immobilized S—Trt Mercaptoethyl Amine on TGS Resin

A suspension of $PPh_3Br_2$ (305 mg, 3 equiv, 0.7 mmol) in DCM (15 mL) was slowly added to a stirred suspension of hydroxymethyl TGS AC resin (1.0 g, 1 equiv, 0.23 mmol) in DCM (10 mL) at RT under argon. After stirring for 3 h at RT, the reaction mixture was filtered, and the resin was washed with DCM (4×15 mL) and dried under vacuum (1.018 g, 99.2%).

A solution of 0.5M S-Trt mercaptoethyl amine hydrochloride (S-trityl-2-aminoethanethiol hydrochloride) (1.732 g) in DMF (8 mL) and DIEA (701 μL) were added to the bromo TGS resin at RT under argon. The reaction mixture was stirred for 18 h at RT, and was washed with MeOH (3×15 mL), DCM (4×15 mL) and dried under vacuum (yield: 1.087 g, 96%).

Example 2

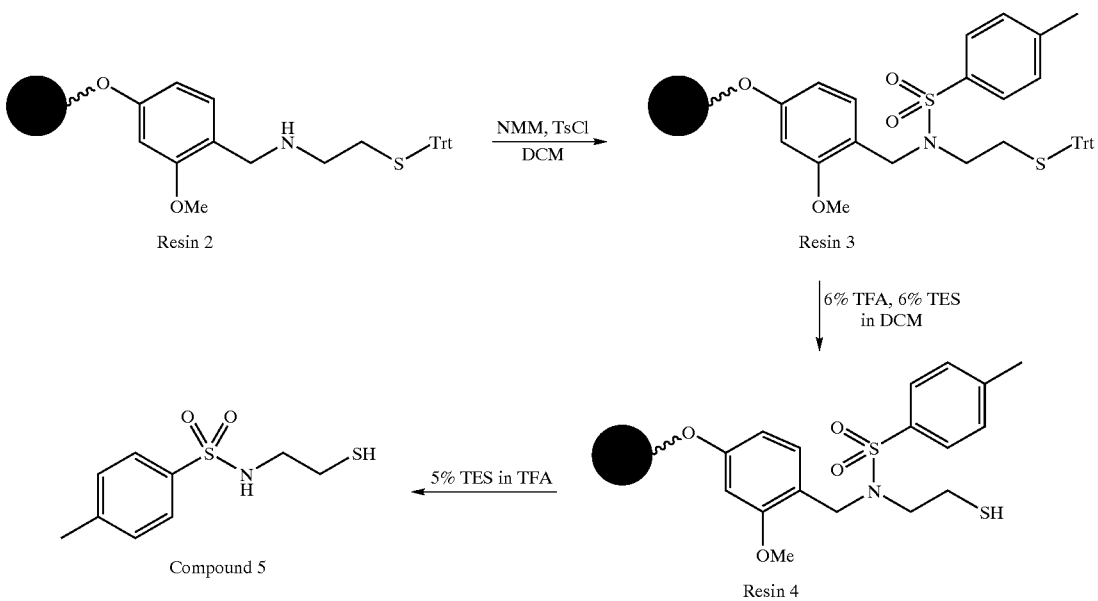

A solution of 1.0M N-methyl morpholine (0.101 g) in DCM (1 mL) and 0.5M p-toluene sulfonyl chloride (95 mg) in DCM (1 mL) were added to resin 2 (100 mg) at RT under argon. After stirring for 18 h, the reaction mixture was washed with MeOH (2×2 mL) and DCM (3×2 mL) to give resin 3.

A solution of 6% TFA and 6% TES in DCM (2 mL) was added to resin 3 at RT under argon. After stirring for 1 h, reaction mixture was washed with DCM (3×2 mL) to give resin 4. Resin 4 was then treated with 5% TES in TFA for 1 h at RT under argon and the resulting mixture was filtered, the filtrate collected and TFA removed under vacuum to give compound 5 (yield: 3.87 mg, 73%). $^1$H NMR (300 MHz, CDCl$_3$): 2.41 (s, 3H); 2.61 (q, 2H); 3.17(q, 2H); 4.86(s, 1H); 7.37(d, 2H); 7.78(d, 2H).

Example 3

Example 4

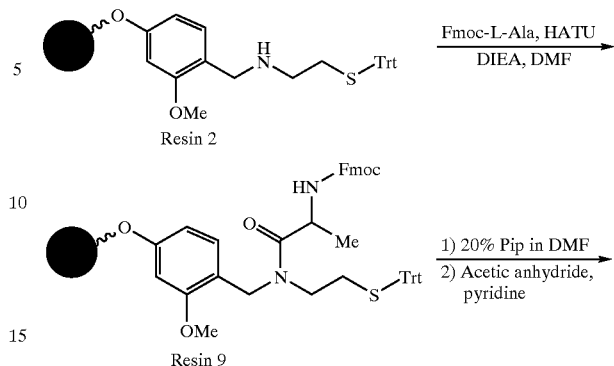

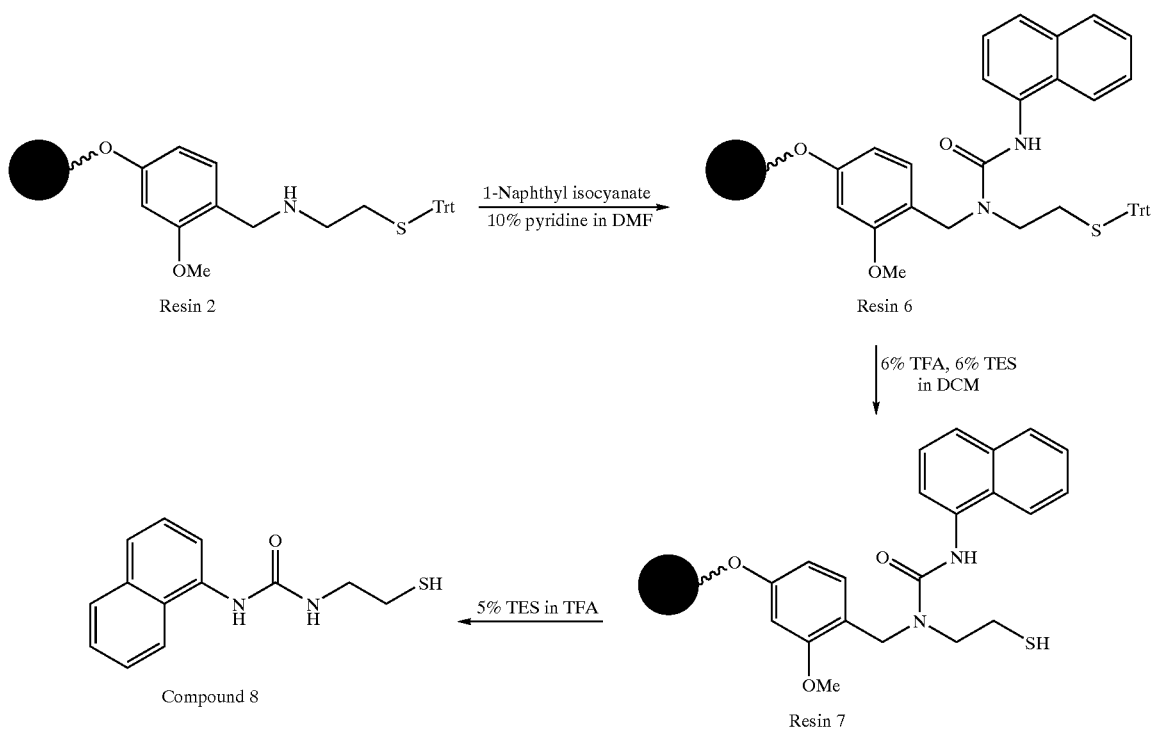

A solution of 1.0M Naphthyl isocyanate (0.338 g) in 10% pyridine/DMF (2 mL) was added to resin 2 (100 mg) at RT under argon. After stirring for 18 h, the reaction mixture was washed with DMF (2×2 mL) and DCM (3×2 mL) to give resin 6.

A solution of 6% TFA and 6% TES in DCM (2 mL) was added to resin 6 at RT under argon. After stirring for 1 h, the reaction mixture was washed with DCM (3×2 mL) to give resin 7.

Resin 7 was then treated with 5% TES in TFA for 1 h at RT under argon and the resulting mixture was filtered, the filtrate collected and TFA removed under vacuum to give compound 8 (yield: 4.2 mg, 75%). $^1$H NMR (300 MHz, DMSO-d$_6$): 2.61(t, 2H); 3.37(q, 2H); 7.61(m, 7H).

-continued

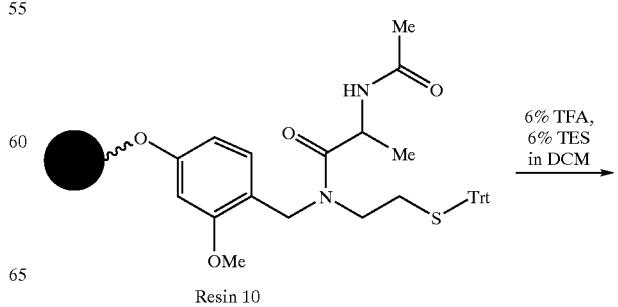

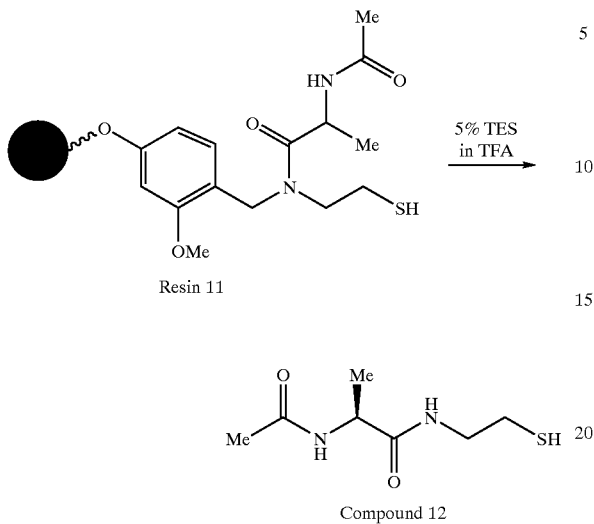

Resin 11

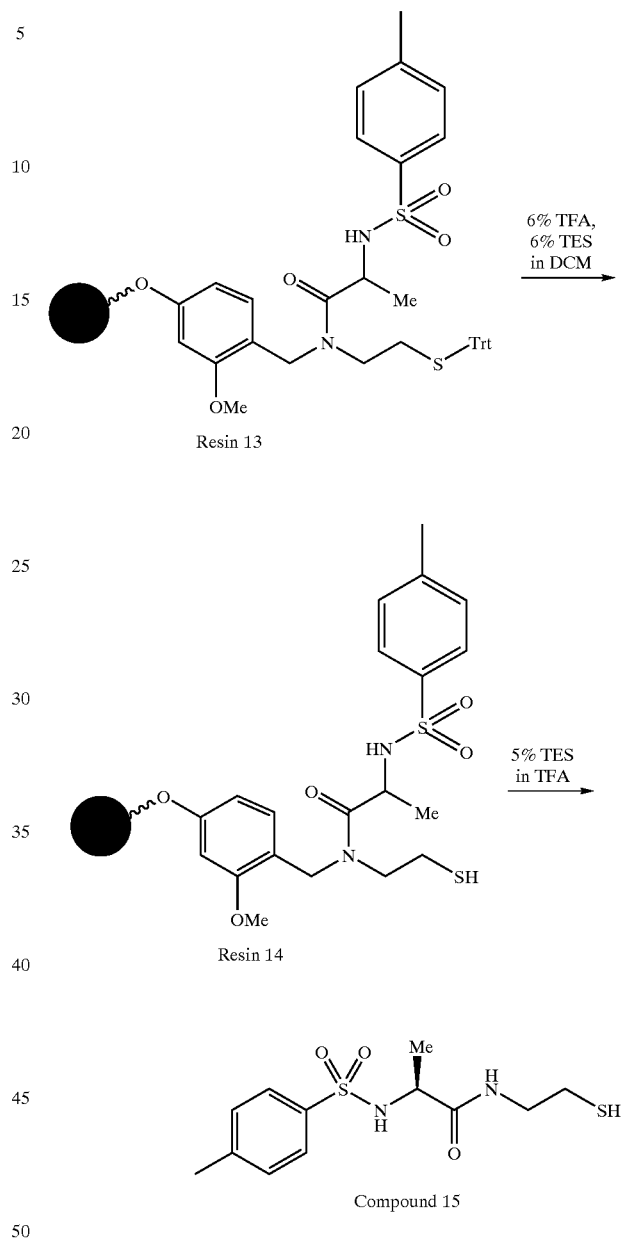

Resin 13

Resin 14

Compound 15

Compound 12

A solution of Fmoc-L-Ala (35 mg, 5 equiv.), HATU (47 mg, 5 equiv.) and DIEA (36 μL, 9 equiv.) in DMF (2 mL) was added to resin 2 (100 mg) at RT under argon. After stirring for 18 h, the reaction mixture was drained and the resin washed with MeOH (2×2 mL) and DCM (3×2 mL) to give resin 9. 20% piperidine in DMF (2 mL) was added to resin 9 and stirred for 20 min, then the piperidine solution was drained and the resin washed with MeOH (2×2 mL) and DCM (3×2 mL). To the resulting resin was added Pyridine (1 mL) and acetic anhydride (1 mL) and the reaction mixture was stirred for 1 h at RT. The crude resin 10 was washed with MeOH (2×2 mL) and DCM (3×2 mL). Deprotection of Trt with 6% TFA, 6% TES in DCM (2 mL) at RT under argon, followed by draining of the reaction mixture and washing the resin with DCM (3×2 mL) yielded resin 11. Resin 11 was then treated with 5% TES in TFA for 1 h at RT under argon and the resulting mixture was filtered, the filtrate collected and TFA removed under vacuum to give compound 12 (yield: 3.1 mg, 71%). $^1$H NMR (300 MHz, CDCl$_3$): 1.38 (d, 3H); 2.02(s, 3H); 2.64(t, 2H); 3.43(q, 2H); 4.43(q, 1H); 6.01(s, 1H); 6.45(s, 1H).

Example 5

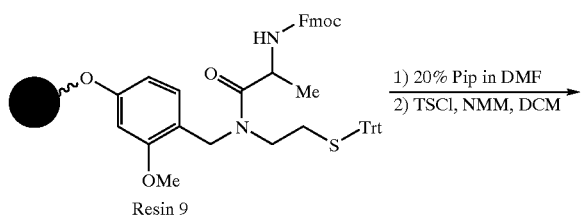

Resin 9

A solution of 20% piperidine in DMF (2 mL) was added to resin 9 and stirred for 20 min. then the resin was washed with MeOH (2×2 mL) and DCM (3×2 mL). To the resulting resin was added 1.0 M N-methyl morpholine (0.101 g) in DCM (1 mL) and 0.5 M p-toluene sulfonyl chloride (95 mg) in DCM (1 mL). The reaction mixture was stirred for 18 h at RT. The crude resin 13 was washed with MeOH (2×2 mL) and DCM (3×2 mL). Deprotection of Trt with 6% TFA, 6% TES in DCM (2 mL) at RT under argon, followed by washing the resin with DCM (3×2 mL) yielded resin 14. Resin 14 was then treated with 5% TES in TFA for 1 h at RT under argon and the resulting mixture was filtered, the filtrate collected and TFA removed under vacuum to give compound 15 (yield: 3.7 mg, 54%). $^1$H NMR (300 MHz, CDCl$_3$): 1.23(d, 3H); 2.42(s, 3H); 2.57(m, 2H); 3.38(q, 2H); 3.77(q, 1H); 4.91(d, 1H); 6.59(s, 1H); 7.35(d, 2H); 7.77(d, 2H).

Example 6

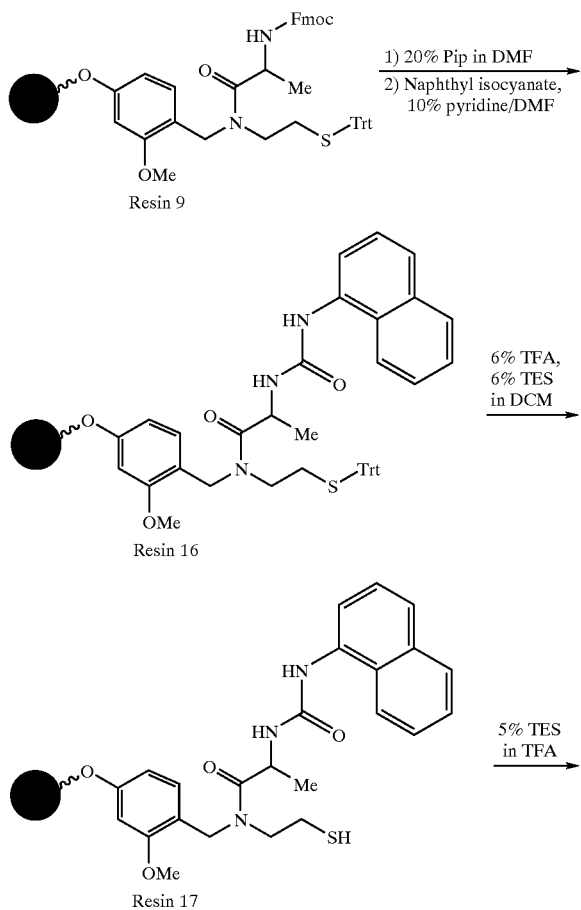

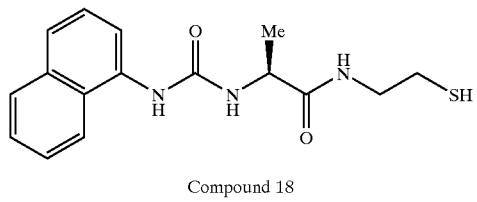

Compound 18

A solution of 20% piperidine in DMF (2 mL) was added to resin 9 and stirred for 20 min, then the resin was washed with MeOH (2×2 mL) and DCM (3×2 mL). To the resulting resin was added 1.0M 1-naphthyl isocyanate (0.338 g) in 10% pyridine/DMF (2 mL). The reaction mixture was stirred for 18 h at RT. Crude resin 16 was washed with MeOH (2×2 mL) and DCM (3×2 mL). Deprotection of Trt with 6% TFA, 6% TES in DCM (2 mL) at RT under argon, followed by washing the resin with DCM (3×2 mL), yielded resin 17. Resin 17 was then treated with 5% TES in TFA for 1 h at RT under argon and the resulting mixture was filtered, the filtrate collected and TFA removed under vacuum to give compound 18 (yield: 3.7 mg, 51%). $^1$H NMR (300 MHz, DMSO-d$_6$): 1.39(d, 3H); 2.63(t, 2H); 3.27(t, 2H); 4.31(q, 1H); 7.73(m, 7H).

Example 7

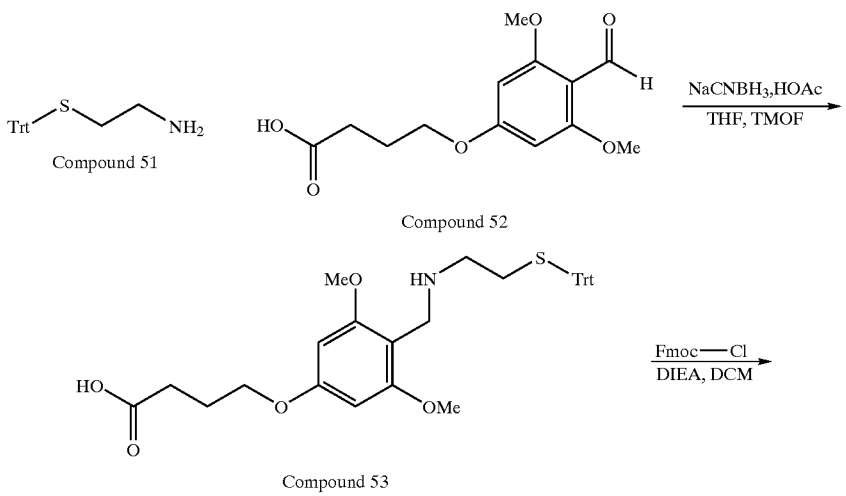

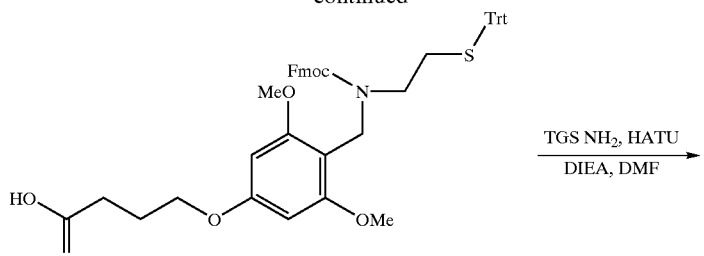

Compound 54

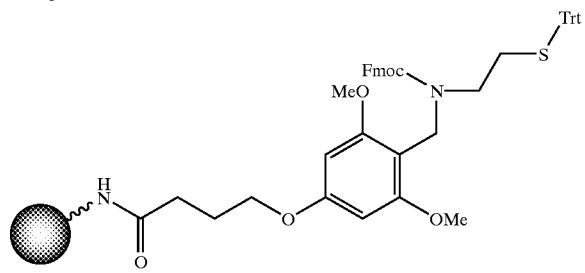

Compound 55

Synthesis of S-Protected Mercaptoamine-Linker-Resin

Compound 53

S-trityl-2-aminoethanethiol (Compound 51) (3.44 g) and Compound 52 (2.6 g, 0.9 equiv.; purchased from PerSeptive Biosystems) in THF (30 mL) and trimethyl orthoformate (TMOF) (5 mL) are stirred for 2 hr at room temperature under nitrogen. Acetic acid (HOAc) (35 μL) and 1 M NaCNBH$_3$ in THF (19.4 mL, 2 equiv.) is added to the mixture and stirred for 18 hr. Solvent is removed under reduced pressure. The crude material is loaded on a silica gel column and eluted with DCM-MeOH-HOAc (99-0.15-0.04).

Compound 54

To Compound 53 (3.11 g) and DIEA (0.948 mL, 2 equiv.) in DCM (20 mL) is added Fmoc-Cl (0.73 g, 1.05 equiv.). The reacture mixture is stirred for 2 hr at room temperature under argon. Solvent is removed under vacuum and the crude oil is redissolved in EtOAc (50 mL) and washed with 0.5 N aqueous HCl (1×50 mL), then H$_2$O (1×50 mL). The organic layer is dried with MgSO$_4$, filtered and solvent removed under vacuum. The crude oil is loaded on a silica gel column and eluted with DCM-MeOH-HOAc (99-0.08-0.02).

Compound 55

Compound 54 (1.05 g, 1.1 equiv.), HATU (502 mg, 1.1 equiv.) and DIEA (694 μL, 3.3 equiv.) are added to TentaGel S NH$_2$ resin (5 g, 0.24 mmole/g) in DMF (5 mL); the reaction mixture is then shaken for 5 hr. The resin is filtered and washed with MeOH (3×8 mL) and THF (3×8 mL). The resin is dried under vacuum to give compound 55.

Example 8

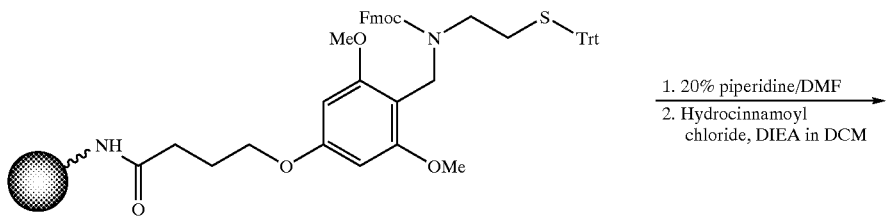

Compound 55

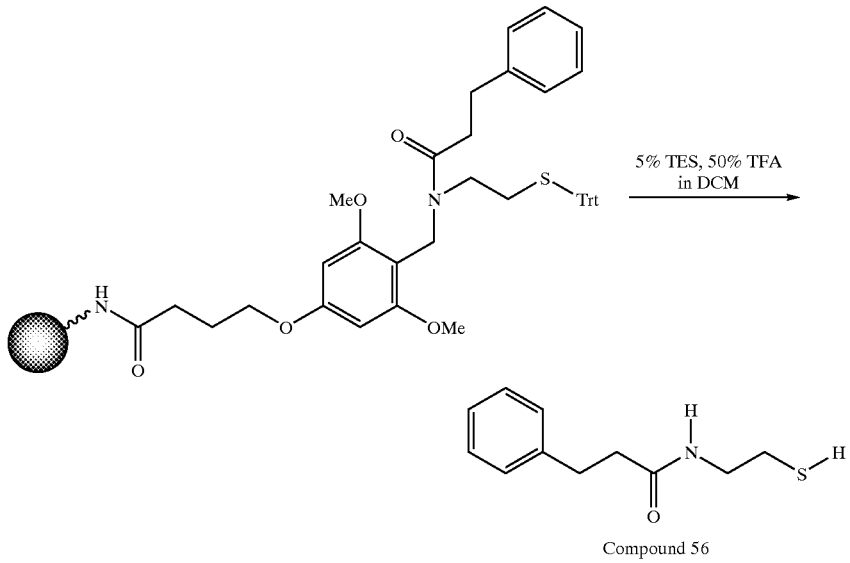

Compound 56

Derivatization of Resin-Bound S-Protected Mercaptoamine

Preparation of Compound 56

Compound 55 from Example 7 (300 mg) in 20% piperidine/DMF (5 mL) is shaken for 20 min. The resin is washed with MeOH (3×5 mL) and DCM (2×5 mL). DIEA (126 μL, 10 equiv.) and hydrocinnamoyl chloride (53.4 μL, 5 equiv) in DCM (5 mL) are added at room temperature under nitrogen. The reaction mixture is shaken for 18 hr. The resin is then washed with MeOH (3×5 mL) and DCM (2×5 mL).

5% TES, 50% TFA in DCM is then added to the resin and shaken for 1 hr. The resin is filtered; the filtrate is removed and the solvent evaporated to give compound 56.

Example 9

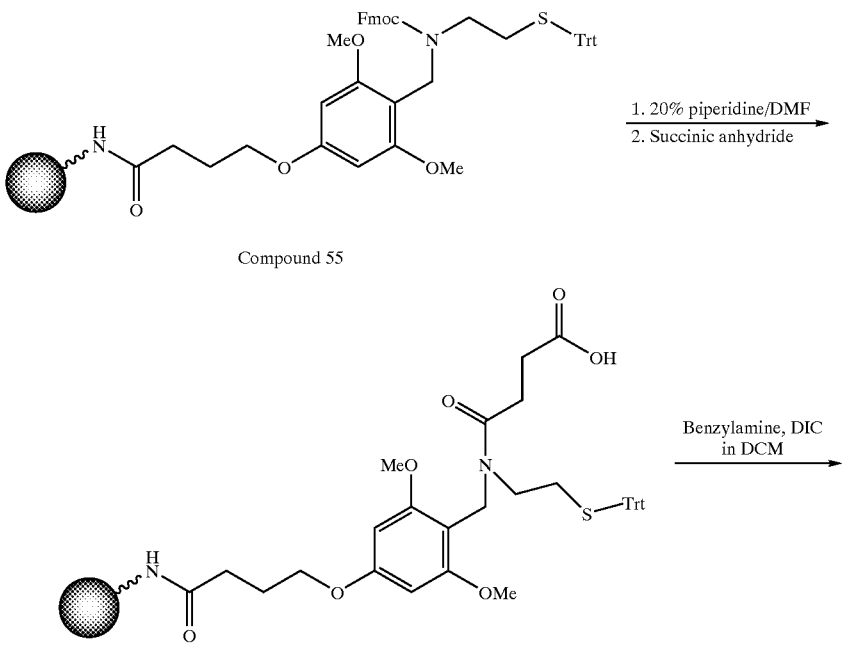

Compound 55

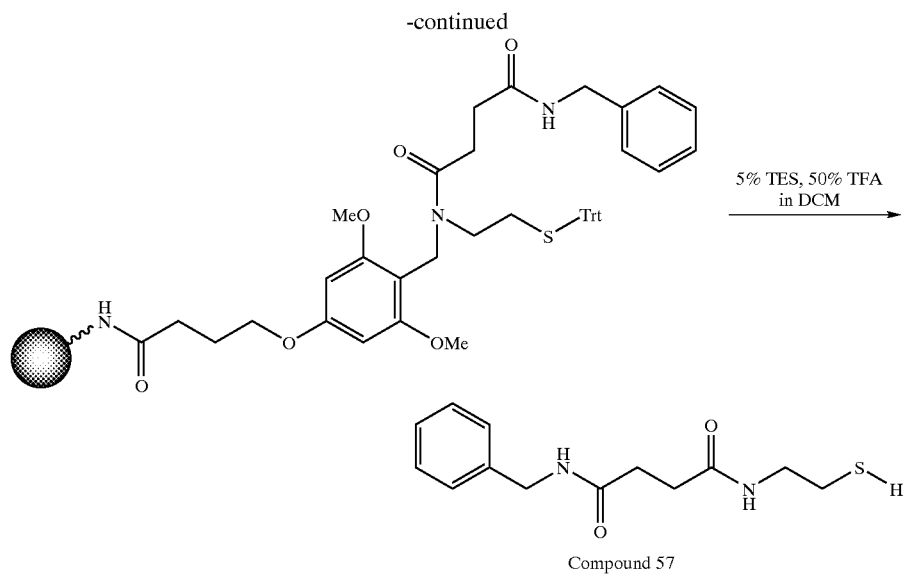

Compound 57

Derivatization of Resin-Bound S-Protected Mercaptoamine

Preparation of Compound 57

Compound 55 from Example 7 (300 mg) in 20% piperidine/DMF (5 mL) is shaken for 20 min. The resin is washed with MeOH (3×5 mL) and DCM (2×5 mL). 1 M succinic anhydride in DMF (5 mL) is added to the resin at room temperature under nitrogen, and the reaction mixture shaken for 18 hr. The resin is washed with MeOH (3×5 mL) and DCM (2×5 mL).

Benzyl amine (78.6 µl, 10 equiv.) and DIC (113 µl, 10 equiv.) are added to the resin in DCM (5 mL). The reaction mixture is shaken for 18 hr at room temperature under nitrogen. The resin is washed with MeOH (3×5 mL) and DCM (2×5 mL).

5% TES, 50% TFA in DCM is added to the resin and shaken for 1 hr. The resin is filtered; the filtrate is removed and evaporated to give compound 57.

Example 10

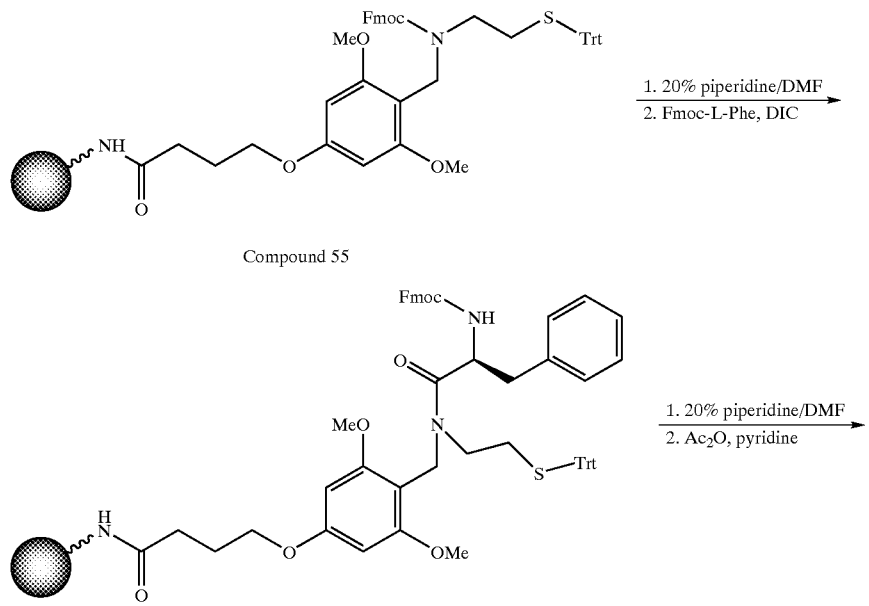

Compound 55

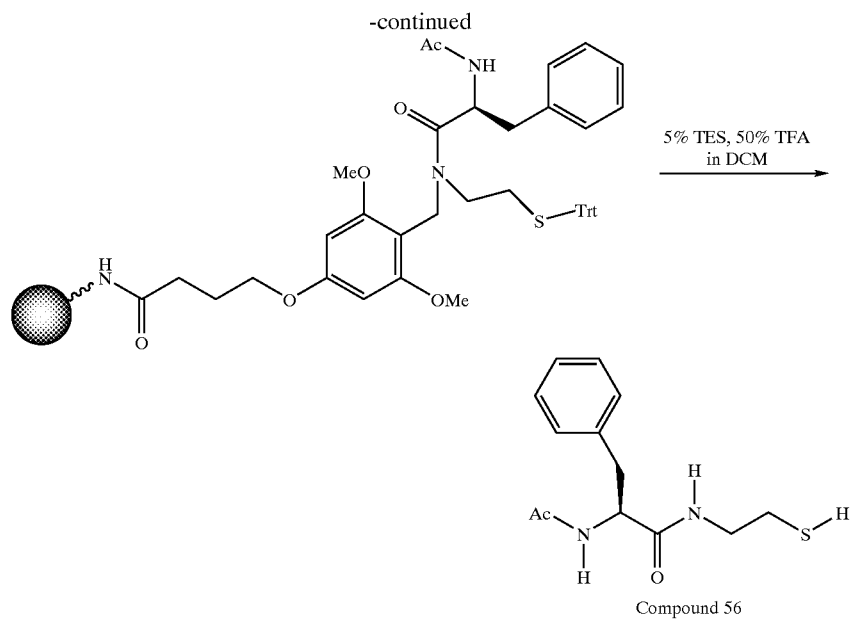

Derivatization of Resin-Bound S-Protected Mercaptoamine

Preparation of Compound 58

Compound 55 from Example 7 (300 mg) in 20% piperidine/DMF (5 mL) is shaken for 20 min. The resin is washed with MeOH (3×5 mL) and DCM (2×5 mL). Fmoc-L-Phe (280 mg, 10 equiv.) and DIC (56 µL, 5 equiv.) are added to the resin in DMF (5 mL) at room temperature under nitrogen. The reaction mixture is shaken for 18 hr. The resin is washed with MeOH (3×5 mL) and DCM (2×5 mL).

20% Piperidine/DMF (5 mL) is added to the resin and the reaction mixture shaken for 20 min. The resin is washed with MeOH (3×5 mL) and DCM (2×5 mL).

Pyridine (2 mL) and acetic anhydride (1 mL) are added to the resin and shaken for 2 hr. The resin is washed with MeOH (3×5 mL) and DCM (2×5 mL).

5% TES, 50% TFA in DCM is added to the resin and shaken for 1 hr. The resin is filtered; the filtrate is removed and evaporated to give compound 58.

Example 11

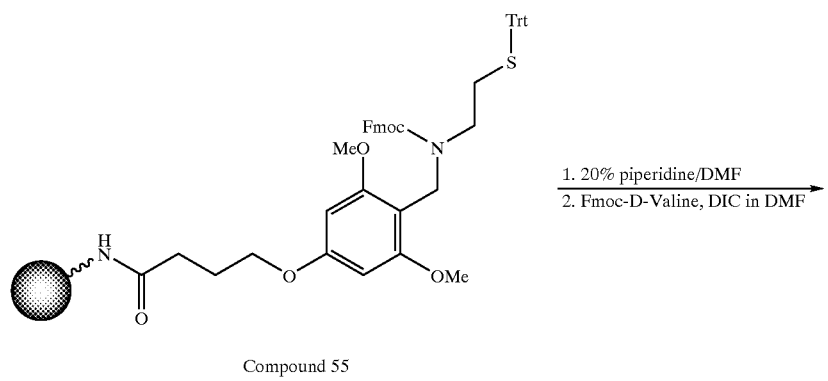

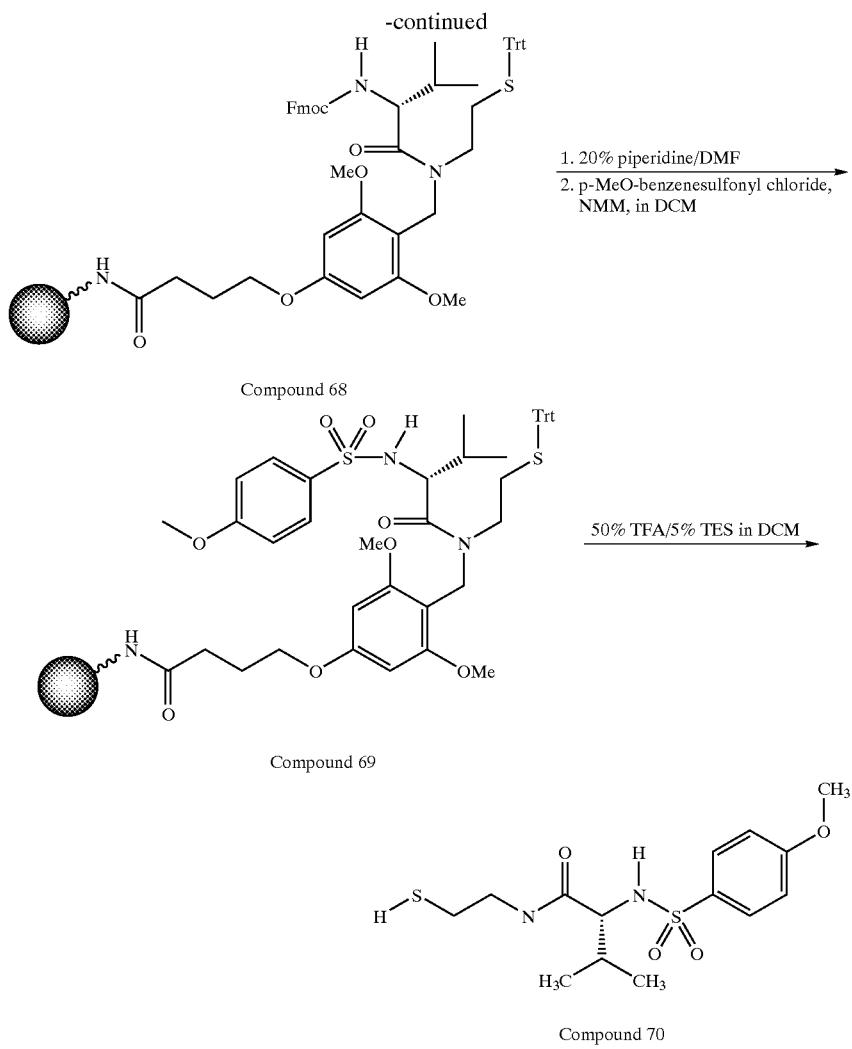

Compound 68

Compound 69

Compound 70

Synthesis of Compound 70

Compound 55 from Example 7 (300 mg) is shaken with 20% piperidine in DMF (5 mL) for 20 min. The resin is washed with MeOH (3×5 mL) and DCM (2×5 mL). Fmoc-D-Valine (203 mg, 10 equiv.) and DIC (diisopropylcarbodiimide) (47 μL, 5 equiv.) are added to the resin in DMF (5 mL) at room temperature under nitrogen. The reaction mixture is shaken for 18 hr. The resin is washed with MeOH (3×5 mL) and DCM (2×5 mL) to yield Compound 68.

Compound 68 (300 mg) is shaken with 20% piperidine in DMF (5 mL) for 20 minutes. The resin is washed with MeOH (3×5 mL) and DCM (2×5 mL). Then N-methylmorpholine (132 μL, 20 equiv.) and 4-methoxybenzenesulfonyl chloride (124 mg, 10 equiv.) in DCM are added to the resin at room temperature and the reaction mixture shaken for 4 hr. The resin is washed with MeOH (3×5 mL) and DCM (2×5 mL) to yield Compound 69.

5% TES, 50% TFA in DCM is added to the resin and the resin shaken for 1 hr. The resin is filtered and the solvent is removed from the filtrate to yield Compound 70.

Example 12

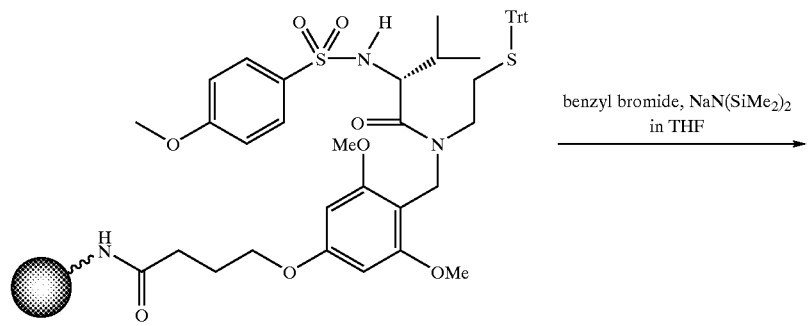

Compound 69

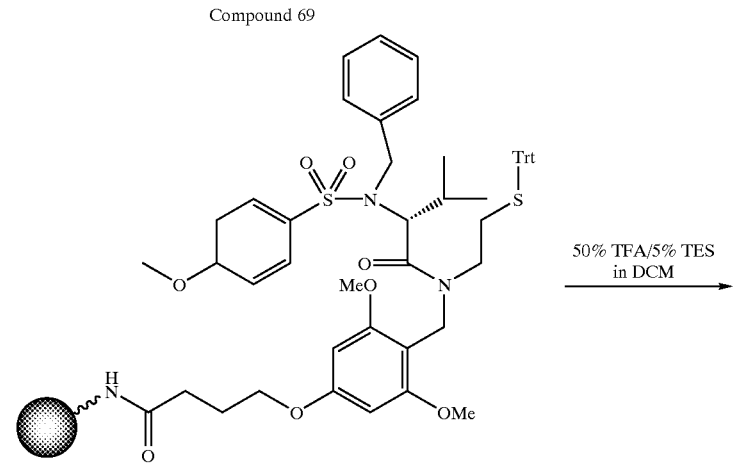

Compound 71

Synthesis of Compound 71

To Compound 69 from Example 11 (300 mg) in THF (5 mL) is added 1 M sodium bis(trimethylsilyl)amide in THF (1.2 mL, 20 equiv.) and benzyl bromide (143 μL, 20 equiv.) at room temperature under argon. The reaction mixture is shaken for 18 hr. The resin is washed with MeOH (3×5 mL) and DCM (2×5 mL). Then 5% TES, 50% TFA in DCM is added to the resin and the resin shaken for 1 hr. The resin is filtered and the solvent is removed from the filtrate to yield Compound 71.

Example 13

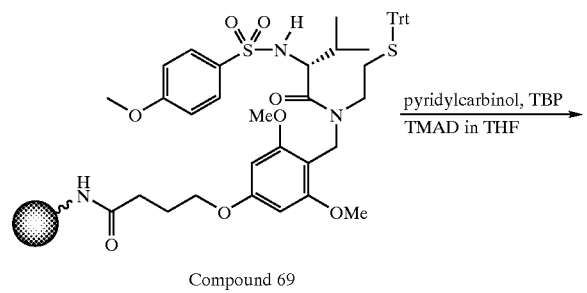

Compound 69

-continued

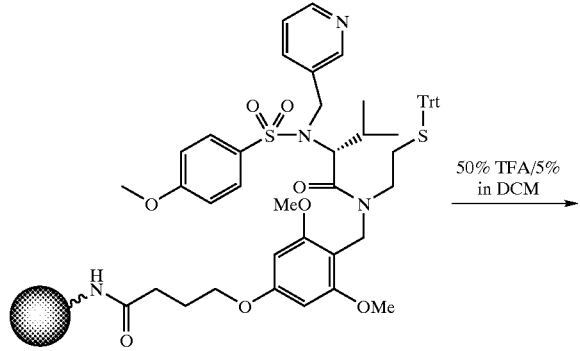

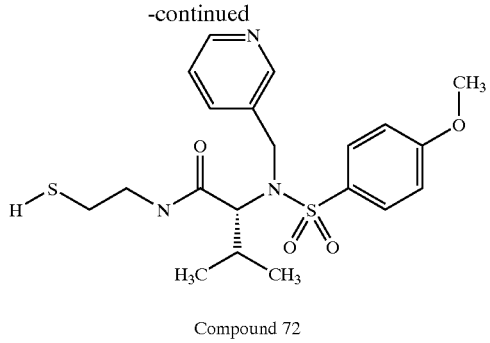

Compound 72

Synthesis of Compound 72

To Compound 69 from Example 11 (300 mg) in THF (4 mL) is added tributylphosphate (404 mg, 0.5 M), pyridyl-carbinol (388 μL, 1.0 M), and N,N,N',N'-tetramethylazodicarboxamide (344 mg, 0.5 M) at room temperature under argon. The reaction is shaken for 18 hr. The resin is washed with MeOH (3×5 mL) and DCM (2×5 mL). Then 5% TES, 50% TFA in DCM is added to the resin and the resin shaken for 1 hr. The resin is filtered and the solvent is removed from the filtrate to yield Compound 72.

Example 14

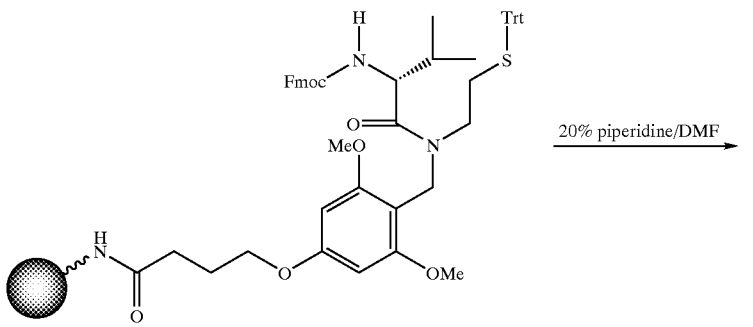

Compound 68

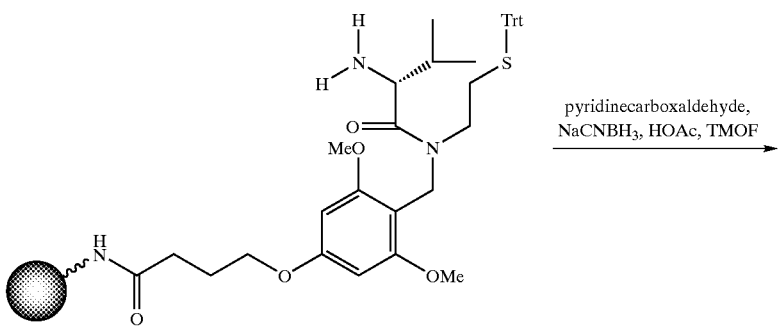

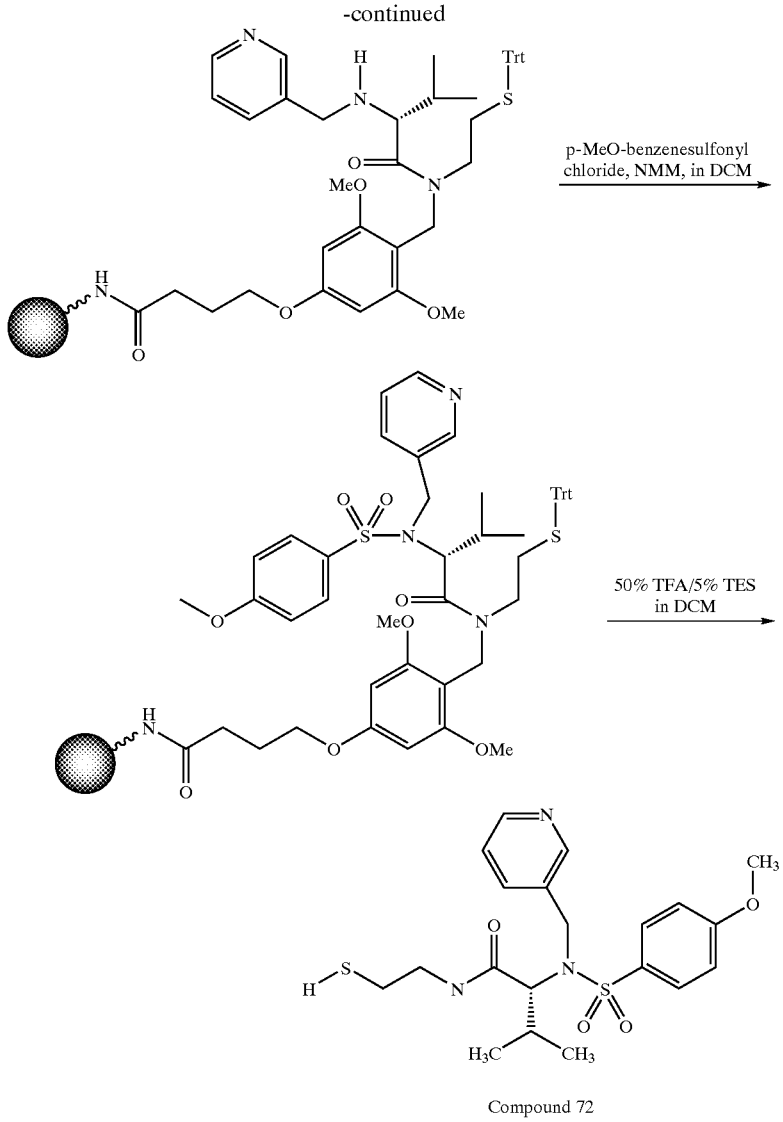

Compound 72

Alternate Synthesis of Compound 72

To Compound 68 from Example 11 (300 mg) is added 20% piperidine in DMF (5 mL). The resin is shaken for 20 minutes, then washed with MeOH (3×5 mL) and DCM (2×5 mL). Pyridinecarboxaldehyde (113 μL, 20 equiv.) in trimethyl orthoformate (5 mL) is stirred for 30 min. at room temperature under nitrogen. HOAc (100 μL, 2%) and 1 M NaCNBH₃ in THF (1.8 mL, 30 equiv.) are added to the reaction mixture and stirred for 18 hr. The resin is washed with MeOH (3×5 mL) and DCM (2×5 mL).

N-methylmorpholine (132 μL, 20 equiv.) and 4-methoxybenzene sulfonyl chloride (124 mg, 10 equiv.) are added to the resin at room temperature. The reaction is shaken for 4 hr. and the resin washed with MeOH (3×5 mL) and DCM (2×5mL).

5% TES, 50% TFA in DCM is added to the resin and the resin shaken for 1 hr. The resin is filtered and the solvent is removed from the filtrate to yield Compound 72.

Example 15

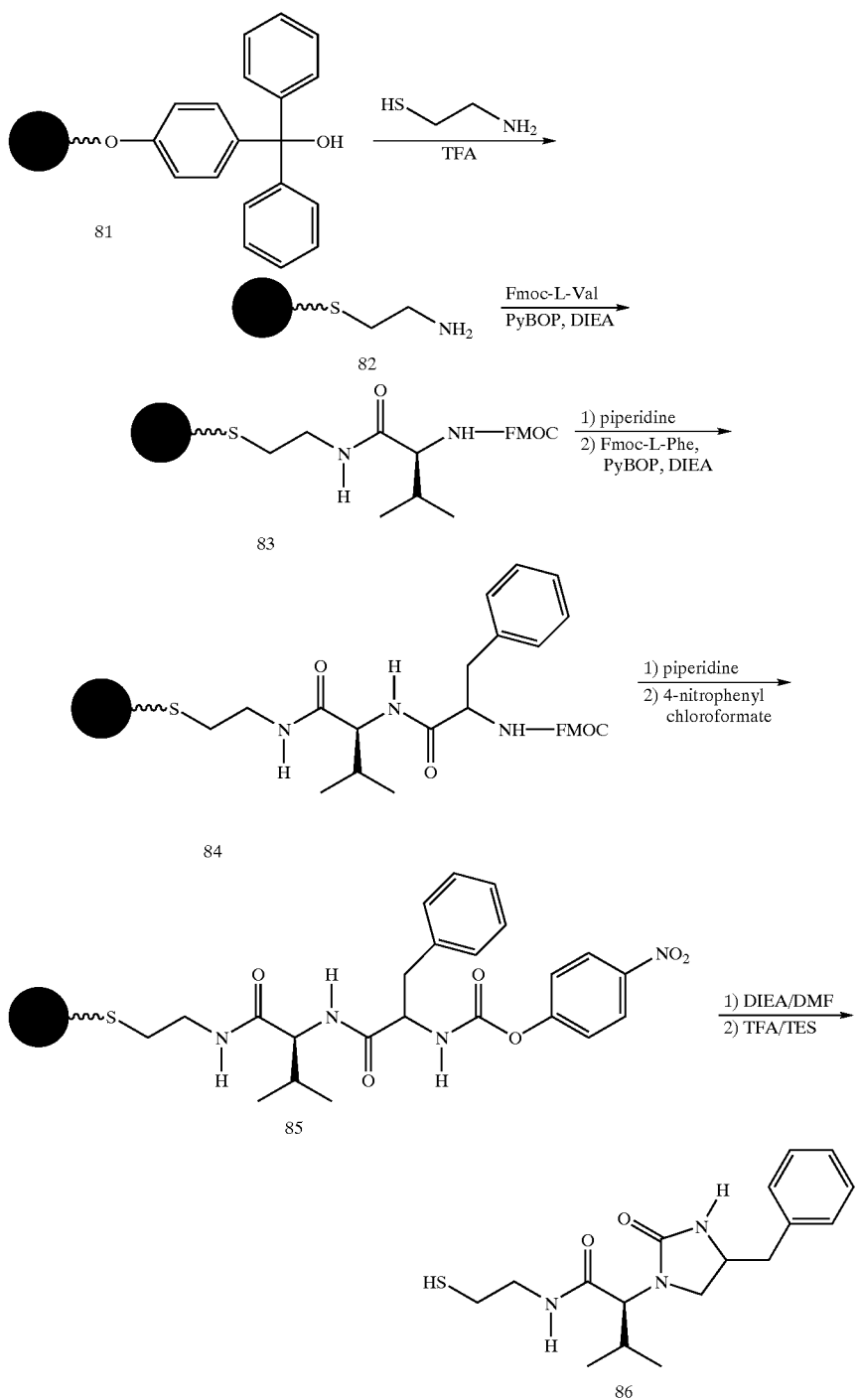

A suspension of resin 81 (trityl alcohol resin, Novabiochem, San Diego, Calif.) (300 mg, 0.24 mmol/g) was stirred with 2-aminoethanethiol hydrochloride (82 mg, 10 equivalents) in TFA (5 mL) for 30 min. TFA was removed under reduced pressure and the resin was washed with ethyl ether (2×5 mL), MeOH (2×5 mL) and THF (3×5 mL). The resin was dried under vacuum to give resin 82.

To resulting resin 82 was added Fmoc-L-Val (122 mg, 5 eq.), DIEA (189 μL, 15 eq.) and PyBOP (187 mg, 5 eq.) in DMF (4 mL). The reaction mixture was shaken for 2 hr., then washed with MeOH (2×5 mL) and DCM (3×5 mL) to give resin 83.

A solution of 20% piperidine in DMF (4 mL) was added to the resin and the mixture was shaken for 20 min. The resin was washed with MeOH (2×5 mL) and DCM (3×5 mL). A mixture of Fmoc-L-Phe (139 mg, 5 eq.), DIEA (189 μL, eq.) and PyBOP (187 mg, 5 eq.) in DMF (4 mL) was added to the resin. The reaction mixture was shaken for 2 hr., then washed with MeOH (2×5 mL) and DCM (3×5 mL) to give resin 84.

A solution of 20% piperidine in DMF (4 mL) was added to the resin and the mixture was shaken for 20 min. The resin was washed with MeOH (2×5 mL) and DCM (3×5 mL).

To a mixture of the resin and DIEA (126 μL, 10 equiv.) in THF (4 mL) was added 4-nitrophenyl chloroformate (p-NP-Cl) (72 mg, 5 eq.). The reaction mixture was shaken for 18 hours at RT; then the resin was washed with DMF (2×5 mL) and DCM (3×5 mL).

A solution of 10% DIEA in DMF (4 ml) was added to the resin and the mixture was heated at 80° C. overnight. Then the resin was washed with MeOH (2×5 ml) and DCM (3×5 ml).

A solution of 10% TFA and 5% triethylsilane in DCM (4 mL) was then added to the resin and the reaction mixture was shaken for 30 minutes. The resin was filtered; the filtrate was collected and the solvent evaporated under reduced pressure to yield compound 86 (yield: 19.2 mg, 77%).

$^1$H NMR (300 MHz, CD$_3$OD) δ0.97 (d, 6H), 2.58 (m, 3H), 3.04 (m, 2H), 3.29 (m, 2H), 3.96 (d, 1H), 4.43 (t, 1H), 7.23 (m, 5H).

Example 16

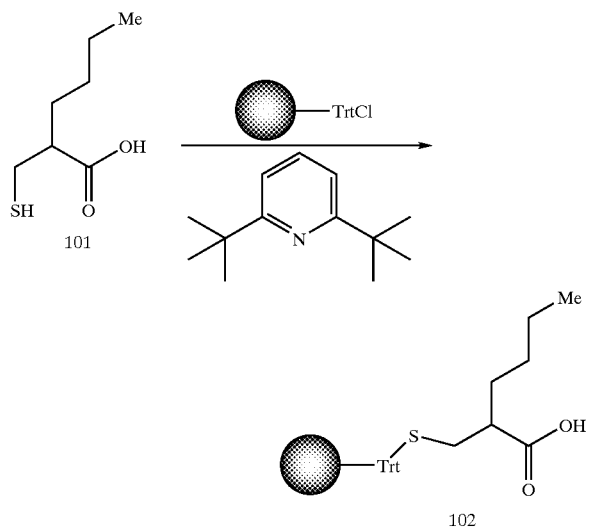

Solid-Phase Synthesis of Mercapto Compounds: Using Thiol Group as Attachment Point to Resin 2-Butyl-3-mercaptanpropionic acid (101) was added to a suspension of 2-chlorotritylchloride resin (Novabiochem, San Diego, Calif.; 200–400 mesh, 1.05 mmol/g, 2 g) in dry DMF (15 mL), followed by addition of di-tert-butyl pyridine (5 mL). The mixture was shaken at room temperature for 18 h. The resin was washed sequentially with DMF and DCM (6 times), and dried overnight under vacuum, to yield 102.

Example 17

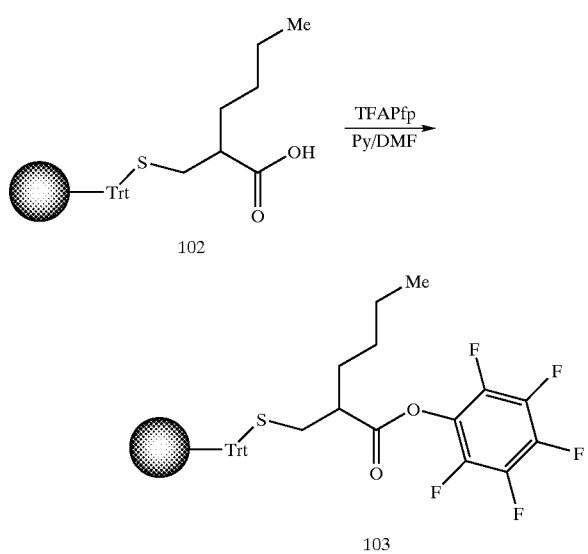

Activation of Resin-Bound Carboxylic Acid

To the immobilized mercaptocarboxylic acid on resin from Example 16 (102) (1 g, 1 mmol) in DMF (5 mL) and pyridine (2 ml) was added pentafluorophenyl trifluoroacetate (TFAPfp) (1.7 mL, 10 mmol) at room temperature. The mixture was shaken at room temperature for 18 h. The resin 103 was washed sequentially with DMF and DCM (6 times), and dried under vacuum.

Example 18

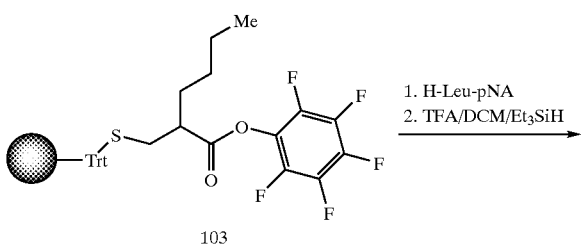

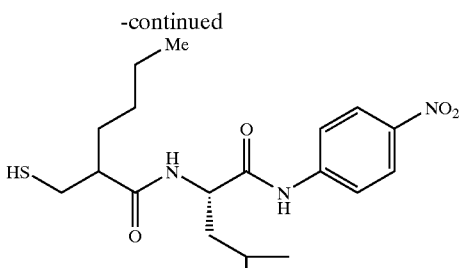

110

Synthesis of Compound 110

62 mg of resin 103 from Example 17 was reacted with a solution of leucine p-nitroanilide (H-Leu-pNA) (151 mg, 0.6 mmol, 10 eq) in 1 mL of pyridine/DCM (10% v/v) at room temperature overnight, after which the resin was washed sequentially with DMF and DCM (6 times). A solution of TFA/DCM (5% v/v, 1 mL) was added to the resin, followed by slow addition of Et₃SiH until the purple color of the resin faded. The filtrate was concentrated in vacuo to give crude 110 as a semisolid identified by comparison with authentic sample: NMR (CDCl₃, 300 MHz) 9.35 (d, 1H), 8.12 (d, 2H), 7.65 (m, 2H), 6.04 (t, 1H), 4.65 (m, 1H), 2.78 (m, 1H), 2.30 (m, 1H), 2.33 (m, 1H), 1.9 to 1.4 (m, 8 H), 1.28 (m, 4H), 1.05 to 0.7 ppm(m, 9H); ES-MS (negative mode): 394 (M−1).

Example 19

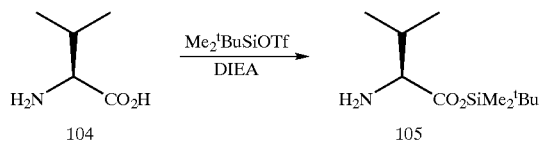

Silylation of Valine—Synthesis of Compound 105

To a suspension of L-valine (1.17 g, 10 mmol) in 10 mL of pyridine/DCM (10%, v/v) was added dimethyl-tert-butylsilyl triflate (Aldrich, 2.18 mL, 9.5 mmol) at room temperature, followed by addition of DIEA (1.7 mL, 10 mmol). The mixture was stirred for 1 h, and the solution of silylated L-valine (105) was used directly without purification.

Example 20

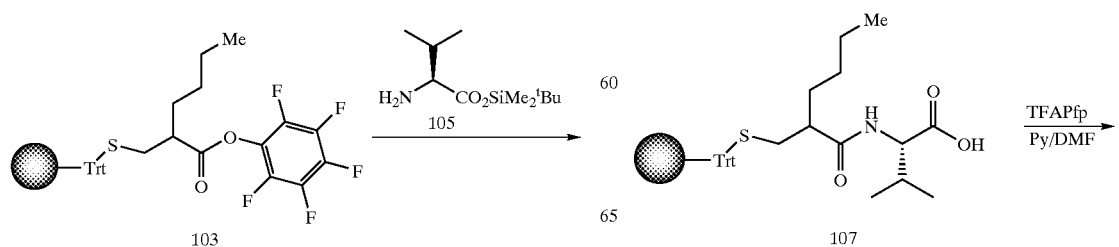

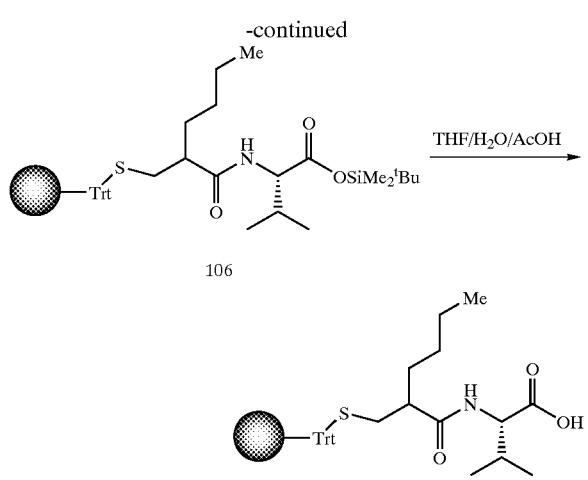

Synthesis of Compound 107

166 mg of resin 103 from Example 17 was reacted with a solution of silylated valine 105 from Example 19 (1 M, 3 mL) in pyridine/DCM (10% v/v) at room temperature for 24 h. The resulting resin 106 was washed sequentially with DMF, water, and DCM (6 times), then treated with a solution of THF:H₂O:AcOH (2:2:1, 3 mL) for 24 h to remove the silyl protecting group. The resin 107 was washed sequentially with DCM, MeOH and DCM (3 times), and dried overnight under vacuum.

Example 21

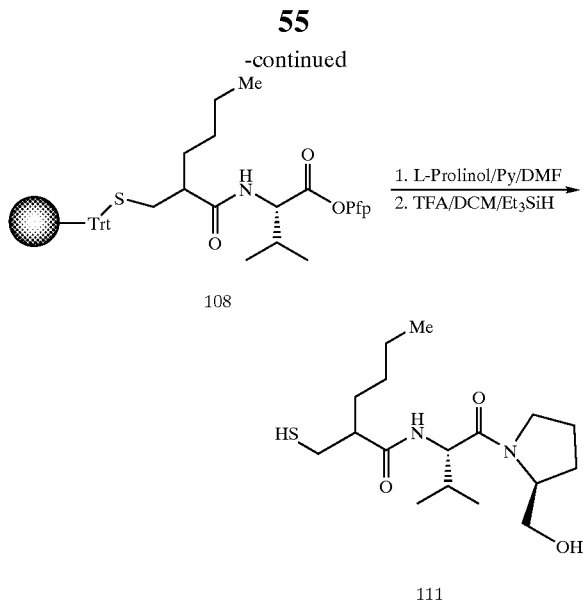

Synthesis of Compound 111

To the resin 107 in DMF (5 mL) and pyridine (1 mL) was added pentafluorophenyl trifluoroacetate (TFAPfP) (0.33 mL, 1.93 mmol) at room temperature. The mixture was shaken at room temperature for 18 h. The resulting resin 108 was washed sequentially with DMF and DCM (6 times), then treated with a solution of L-prolinol (0.34 g, 3.3 mmol) in 0.5 mL of pyridine and 1.5 mL of DMF at room temperature overnight. The resin was then washed sequentially with DMF and DCM (6 times), and dried overnight under vacuum. A solution of TFA/DCM (5% v/v, 2 mL) was added to the resin, followed by slow addition of $Et_3SiH$ until the purple color of the resin faded. Concentration of the filtrate gave an oily residue which was purified by chromatography on silica gel (EtOAc: Hexane=1:1) to give 111 as a mixture of diastereomers (13 mg). NMR ($CDCl_3$, 300 MHz): 6.35 (br, 1H, NH), 4.6 (m), 4.2 (m), 3.3 (m), 2.8 (m), 2.55 (m), 2.3 (m), 2.0 (m), 1.6 (m), 1.22 (br, m), 1.04 to 0.7 ppm (m); ES-MS (negative mode): 343 (M−1).

Example 22

Assays for Peptide Deformylase Activity and Antimicrobial Activity

Continuous Peptide Deformylase Assay

The dipeptide substrate, N-formyl-methionylleucyl-p-nitroanilide (f-ML-pNA) is first deformylated by the peptide deformylase to give the corresponding dipeptide with a free amino terminus, which is a substrate for an aminopeptidase from Aeromonas proteolytica (Sigma Chemical Company). Sequential action by the aminopeptidase releases p-nitroaniline, a chromophore which can be detected spectrophotometrically. Peptide deformylase enzyme is prepared as described in Rajagopalan et al., Biochemistry (1997) 36:13910–13918. The dipeptide substrate is prepared as described in Wei and Pei (1997) Anal. Biochem. 250:29–34. Assays are carried out at 23° C. Assays are performed in polystyrene cuvettes which contain 50 mM potassium phosphate, pH 7.0, 100 µM ethylene glycol bis(b-aminoethyl ether)-N,N'-tetraacetic acid (EGTA), 0 to 200 µM peptide substrate, and 0.8 unit Aeromonas aminopeptidase. Reactions are initiated by addition of 10 to 100 µl (0.1 to 100 µg) of peptide deformylase enzyme diluted in 50 mM Hepes, pH 7.0, 100 µg/ml bovine serum albumin. Reactions are monitored continuously at 405 nm in a Perkin-Elmer λ3 UV/VIS spectrophotometer, and the initial rates are calculated from the early part of the reaction progression curves (<60 s). Reactions at the lowest and highest substrate concentrations are generally repeated with doubled amount of the aminopeptidase (1.6 U) to insure that the peptide deformylase reaction is rate-limiting in the coupled reaction sequence.

Discontinuous Deformylase Assay

Discontinuous reactions are carried out in a buffer containing 50 mM potassium phosphate, pH 7.0, 100 µM EGTA, and 0 to 200 µM peptide substrate (total volume 250 or 500 µl). The reaction is initiated by the addition of 0 to 90 ng of freshly thawed deformylase and allowed to proceed at room temperature for 1 minute. The reaction is terminated by heating to 95° C. for 5 minutes in a hot water bath. The deformylated peptides are completely hydrolyzed by incubation with 0.4 U of Aeromonas aminopeptidase at room temperature for 2 hours. The amount of p-nitroaniline released is determined by measuring its absorbance at 405 nm. The substrate to product conversion is kept at <20% for all deformylase reactions.

Assay Protocol for Antimicrobial Activity. Minimum inhibitory concentrations (MICs) are determined using the microdilution method in 96-well format plates. Compounds are suspended in DMSO at 5 or 10 mg/ml and stored at 4° C. until used. They are diluted in Mueller-Hinton Broth (MHB) or Trypticase Soy Broth (TSB) and used for MIC determination. The range of concentrations tested is 64–0.0625 µg/ml final concentration using a two-fold dilution system.

The inoculum is prepared from cells grown on Trypticase Soy Agar (TSA) and incubated overnight at 35° C., 5 to 10 colonies are used to inoculate MHB or TSB broths, and the culture is incubated overnight at 35° C. The overnight culture is diluted 1:10, incubated for one hour at 35° C., diluted to the appropriate inoculum size and applied to the wells containing broth and test compound. Inoculum sizes are $1\times10^5$ to $5\times10^5$ CFU/ml.

Plates are incubated at 35° C. for 48 hours and MIC are recorded after 18 hours of incubation for bacteria. MIC is defined as the lowest concentration of compound that does not produce visible growth after incubation.

Using these assays, the values of $IC_{50}$, for Compound 110 of Example 18 and Compound 111 of Example 21 against peptide deformylase were determined to be less than 10 µM. Both compounds were tested as a 1:1 mixture of diastereomers.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

What is claimed is:

1. A method of inhibiting a peptide deformylase, the method comprising contacting the peptide deformylase with one or more compounds in an amount effective to inhibit the peptide deformylase, wherein the compound or compounds have the formula:

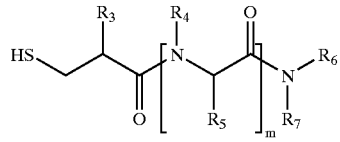

wherein each of $R_3$, $R_4$, $R_5$, $R_6$, and $R_7$ are independently selected from the group consisting of H, alkyl, heteroalkyl, aryl, heteroaryl, and heterocyclic moieties, and amino acid side chains, and wherein m is an integer from 0 to 5;

or a salt thereof.

2. The method of claim 1, wherein the compound has the structure:

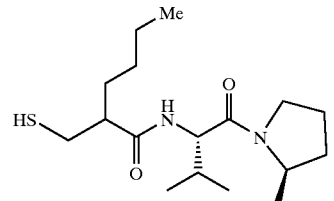

or a salt thereof.

3. The method of claim 1, wherein the compound has the structure:

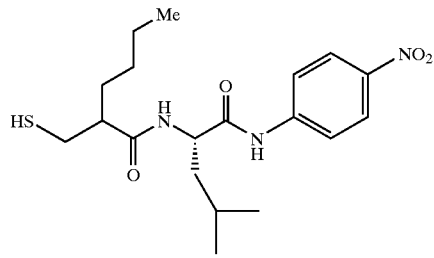

or a salt thereof.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Homo sapiens
<220> FEATURE:
<221> NAME/KEY: VARIANT
<222> LOCATION: (1)...(5)
<223> OTHER INFORMATION: Xaa = Any Amino Acid

<400> SEQUENCE: 1

His Glu Xaa Xaa His
 1               5